US010837909B2

(12) United States Patent
Urano et al.

(10) Patent No.: US 10,837,909 B2
(45) Date of Patent: Nov. 17, 2020

(54) SUPER-RESOLUTION FLUORESCENT IMAGING PROBE

(71) Applicant: The University of Tokyo, Tokyo (JP)

(72) Inventors: Yasuteru Urano, Tokyo (JP); Mako Kamiya, Tokyo (JP); Akihiko Morozumi, Tokyo (JP); Shinnosuke Uno, Tokyo (JP); Keitaro Umezawa, Tokyo (JP)

(73) Assignee: The University of Tokyo, Tokyo (JP)

( * ) Notice: Subject to any disclaimer, the term of this patent is extended or adjusted under 35 U.S.C. 154(b) by 125 days.

(21) Appl. No.: 15/551,149

(22) PCT Filed: Feb. 23, 2016

(86) PCT No.: PCT/JP2016/055199
§ 371 (c)(1),
(2) Date: Aug. 15, 2017

(87) PCT Pub. No.: WO2016/136718
PCT Pub. Date: Sep. 1, 2016

(65) Prior Publication Data
US 2018/0052109 A1 Feb. 22, 2018

(30) Foreign Application Priority Data

Feb. 27, 2015 (JP) .................................. 2015-037519

(51) Int. Cl.
| | |
|---|---|
| *A61B 5/00* | (2006.01) |
| *A61B 8/00* | (2006.01) |
| *A61B 10/00* | (2006.01) |
| *G01N 21/64* | (2006.01) |
| *C09K 11/06* | (2006.01) |
| *G01N 33/68* | (2006.01) |
| *G01N 33/533* | (2006.01) |
| *A61K 49/00* | (2006.01) |
| *G02B 21/00* | (2006.01) |
| *G02B 27/58* | (2006.01) |

(52) U.S. Cl.
CPC ....... *G01N 21/6458* (2013.01); *A61K 49/005* (2013.01); *A61K 49/0019* (2013.01); *C09K 11/06* (2013.01); *G01N 21/6428* (2013.01); *G01N 33/533* (2013.01); *G01N 33/68* (2013.01); *A61K 49/0041* (2013.01); *C09K 2211/1007* (2013.01); *C09K 2211/1011* (2013.01); *C09K 2211/1029* (2013.01); *C09K 2211/1074* (2013.01); *C09K 2211/1096* (2013.01); *G01N 2021/6439* (2013.01); *G02B 21/0076* (2013.01); *G02B 27/58* (2013.01)

(58) Field of Classification Search
None
See application file for complete search history.

(56) References Cited

U.S. PATENT DOCUMENTS

| | | | |
|---|---|---|---|
| 9,329,184 B2 * | 5/2016 | Nagano | ............... C07F 7/0812 |
| 2008/0032414 A1 | 2/2008 | Zhuang et al. | |

(Continued)

FOREIGN PATENT DOCUMENTS

| | | |
|---|---|---|
| JP | 2014157150 | 8/2014 |
| WO | 2012111818 | 8/2012 |

(Continued)

OTHER PUBLICATIONS

Written Opinion dated Apr. 12, 2016 corresponding to International Patent Application No. PCT/JP2016/055199; 8 pages.
M. Fernandez-Suarez et al., Nat. Rev. Mol. Cell. Biol., 9, 929, 2008.
International Search Report dated Apr. 12, 2016 corresponding to International Patent Application No. PCT/JP2016/055199; 8 pages.

*Primary Examiner* — Michael G. Hartley
*Assistant Examiner* — Melissa J Perreira
(74) *Attorney, Agent, or Firm* — Leason Ellis LLP

(57) ABSTRACT

[Problem] To provide a novel fluorescent probe for super-resolution imaging that uses fluorescent light emission characteristics that originate from an intermolecular nucleophilic addition-dissociation equilibrium reaction, and to provide a super-resolution fluorescent imaging method that uses the probe. [Solution] A fluorescent probe for super-resolution imaging that comprises a compound represented by formula (I) or a salt thereof [in the formula, X represents an oxygen atom, $C(R^a)(R^b)$, or $Si(R^a)(R^b)$ (wherein $R^a$ and $R^b$ each independently represent a hydrogen atom or an alkyl group), $R^1$ represents a hydrogen atom or an optionally substituted aryl (provided that, if $R^1$ is a phenyl group, the benzene ring of the phenyl group does not have a substituent at position 2 or position 6), $R^2$ and $R^3$ each independently represent 1-3 identical or differing substituents that are independently selected from the group that consists of hydrogen atoms, hydroxyl groups, halogen atoms, optionally substituted alkyl groups, optionally substituted sulfo groups, optionally substituted carboxyl groups, optionally substituted ester groups, optionally substituted amide groups, and optionally substituted azide groups, $R^4$ and $R^5$ each independently represent a hydrogen atom or an optionally substituted alkyl group or $N(R^4)(R^5)$ forms an amide group or a carbamate group (provided that, if $R^4$ or $R^5$ is an alkyl group, each may form, together with $R^2$, a ring structure that contains the nitrogen atom that is bonded thereto), and $R^6$ and $R^7$ each independently represent a hydrogen atom or an optionally substituted alkyl group or $N(R^6)(R^7)$ forms an amide group or a carbamate group (provided that, if $R^6$ or $R^7$ is an alkyl group, each may form, together with $R^3$, a ring structure that contains the nitrogen atom that is bonded thereto)], the fluorescent probe for super-resolution imaging being characterized in that the compound represented by formula (I) or the salt thereof undergoes a nucleophilic addition-dissociation equilibrium reaction with a nucleophilic compound that contains an —SH group.

10 Claims, 9 Drawing Sheets

(56) References Cited

U.S. PATENT DOCUMENTS

2011/0318788 A1* 12/2011 Coleman .............. C07D 219/08
                                                      435/91.5
2014/0342384 A1    11/2014 Nagano et al.
2015/0353585 A1    12/2015 Nagano et al.
2017/0044372 A1*   2/2017  Gee ..................... C09B 11/24

FOREIGN PATENT DOCUMENTS

| WO | WO-2013029650 A1 * | 3/2013  | .............. C07F 7/081 |
| WO | 2013126816         | 8/2013  |                           |
| WO | 2014106957         | 10/2014 |                           |
| WO | 2015129705         | 9/2015  |                           |

* cited by examiner

SUPER-RESOLUTION FLUORESCENT IMAGING PROBE

TECHNICAL FIELD

The present invention relates to a novel fluorescent probe for super-resolution imaging that uses fluorescent light emission characteristics produced by an intermolecular nucleophilic addition-dissociation equilibrium reaction, and a super-resolution fluorescent imaging method using the probe.

BACKGROUND ART

In general, a point spreads out to about half a wavelength due to the diffraction of light, and therefore, the spatial resolution of an optical microscope is limited to the Abbe diffraction limit, and it has been thought to be impossible to separate and image two points positioned more closely together than the point spread. However, since the 1990s, there have been a number of reports of techniques for super-resolution imaging at a resolution that exceeds the diffraction limit (e.g., Non-Patent Reference 1 and elsewhere), and, by application to living cells, there is an increasing possibility of capturing biological phenomena that could not be observed by conventional methods.

In single-molecule localization microscopy (SMLM) represented by stochastic optical reconstruction microscopy (STORM), which is a type of super-resolution imaging, and photo-activated localization microscopy (PALM), fluorescent molecules separated by a sufficient distance in a sample are caused to stochastically emit light one molecule at a time, a position of each molecule is accurately specified, and a fluorescence image having a resolution of tens of nanometers can be constructed by superimposition (e.g., Patent Reference 1 and elsewhere).

A commercially available fluorescent dye and/or fluorescent protein are mainly used in such SMLM. However, in order to cause such commercially available organic fluorescent dyes to stochastically emit light, a sample must be excited by a high-intensity laser of about 0.8 kW/cm$^2$ in the presence of about 10 to 100 mM of thiol to produce a triplet or other long-lived state of non-fluorescence, and such conditions are not suitable for imaging living cells.

Also, development of a super-resolution fluorescent imaging method has heretofore primarily involved development from the viewpoint of optical systems and analytical software, and critical development of a fluorescent probe is currently lagging.

PRIOR ART REFERENCES

Patent References

Patent Reference 1: Zhuang et al., US 2008/0032414

Non-Patent References

Non-Patent Reference 1: M. Fernandez-Suarez et al., Nat. Rev. Mol. Cell. Biol., 9, 929, 2008

SUMMARY OF THE INVENTION

Problems to be Solved by the Invention

In view of the above, an object of the present invention is to develop a fluorescent probe compound suitable for super-resolution fluorescent imaging that does not require an additive other than a probe compound, that allows omission of laser irradiation, which was required to place a fluorescent probe in a non-fluorescent state prior to data acquisition, and that functions with low-power laser irradiation, and to provide a super-resolution fluorescent imaging method that is also applicable to living cells. A further object is to provide a technique for super-resolution imaging in multiple colors that allows observation in the same field of view, using the fluorescent probe compound.

Means Used to Solve the Above-Mentioned Problems

As the result of thoroughgoing investigation to solve the above-described problems, the present inventors focused on an intermolecular nucleophilic addition-dissociation equilibrium reaction between glutathione or other —SH group-containing compound, the compound being a nucleophilic compound internally present in a living cell, and a fluorophore having pyronin and a pyronin-like backbone (hereinafter collectively referred to as "pyronin backbone"), and by using the flickering of light produced by the reaction as an operating principle, the present inventors discovered a fluorescent probe molecule enabling super-resolution fluorescent imaging under conditions where application to living cells is also possible. More specifically, it was found that optimizing a dissociation constant and a nucleophilic addition reaction rate in the nucleophilic addition-dissociation equilibrium reaction makes it possible to obtain stochastic light emission suitable for super-resolution fluorescent imaging in a concentration range of glutathione in a living cell without dependence on conventional high-concentration thiol addition or high-intensity laser irradiation. The present invention was perfected on the basis of these findings.

In other words, an aspect of the present invention provides:

(1) a fluorescent probe for super-resolution imaging comprising a compound represented by formula (I) or a salt thereof.

(I)

[Chemical formula 1]

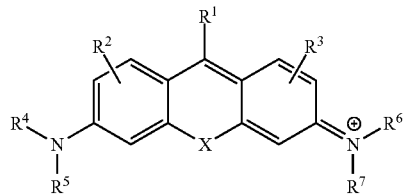

(in the formula, X represents an oxygen atom, C(R$^a$)(R$^b$), or Si(R$^a$)(R$^b$) (wherein R$^a$ and R$^b$ each independently represent a hydrogen atom or an alkyl group); R$^1$ represents a hydrogen atom or an optionally substituted aryl (provided that, when R$^1$ is a phenyl group, a benzene ring of the phenyl group does not have a substituent at position 2 or position 6); R$^2$ and R$^3$ each independently represent one to three identical or differing substituents that are independently selected from the group consisting of a hydrogen atom, a hydroxyl group, a halogen atom, an optionally substituted alkyl group, an optionally substituted sulfo group, an optionally substituted carboxyl group, an optionally substituted ester group, an optionally substituted amide group, and an optionally substituted azide group; $R^4$ and $R^5$ each independently represent a hydrogen atom or an optionally substituted alkyl group, or $N(R^4)(R^5)$ forms an amide group or a carbamate group (in this example, when $R^4$ or $R^5$ is an alkyl group, each may form, together with $R^2$, a ring structure that contains a nitrogen atom that is bonded thereto); and $R^6$ and $R^7$ each independently represent a hydrogen atom or an optionally substituted alkyl group, or $N(R^4)(R^7)$ forms an amide group or a carbamate group (in this example, when $R^6$ or $R^7$ is an alkyl group, each may form, together with $R^3$, a ring structure that contains the nitrogen atom that is bonded thereto)), the fluorescent probe for super-resolution imaging being characterized in that the compound represented by formula (I) or the salt thereof undergoes a nucleophilic addition-dissociation equilibrium reaction with a nucleophilic compound that contains a —SH group;

(2) the fluorescent probe for super-resolution imaging according to the above-described (1), wherein the nucleophilic addition-dissociation equilibrium reaction occurs on a carbon atom to which $R^1$ bonds;

(3) the fluorescent probe for super-resolution imaging according to the above-described (1) or (2), characterized in that a dissociation constant in the nucleophilic addition-dissociation equilibrium reaction is in a range of 0.1 µM to 10 mM;

(4) the fluorescent probe for super-resolution imaging according to any one of the above-described (1) to (3), characterized in that a nucleophilic addition reaction rate constant in the nucleophilic addition-dissociation equilibrium reaction is 1 to $1.0 \times 10^6$ $s^{-1}$ in an aqueous solution having neutral conditions;

(5) the fluorescent probe for super-resolution imaging according to any one of the above-described (1) to (4), wherein X is $C(R^a)(R^b)$ or $Si(R^a)(R^b)$;

(6) the fluorescent probe for super-resolution imaging according to the above-described (5), wherein $R^a$ and $R^b$ are both a methyl group;

(7) the fluorescent probe for super-resolution imaging according to any one of the above-describes (1) to (6), wherein $R^1$ is a hydrogen atom or an optionally substituted phenyl group (provided that a substituent is not present at position 2 or position 6 in the benzene ring of the phenyl group);

(8) the fluorescent probe for super-resolution imaging according to any one of the above-described (1) to (7), wherein $R^4$, $R^5$, $R^6$, and $R^7$ are each a hydrogen atom;

(9) the fluorescent probe for super-resolution imaging according to any one of the above-described (1) to (7), wherein $R^4$, $R^5$, $R^6$, and $R^7$ are each a methyl group;

(10) the fluorescent probe for super-resolution imaging according to any one of the above-described (1) to (7), wherein at least one of $R^4$, $R^5$, $R^6$, and $R^7$ has a labeled substituent capable of covalently or non-covalently bonding to a biomolecule;

(11) the fluorescent probe for super-resolution imaging according to any one of the above-described (1) to (10), wherein the compound containing the —SH group has a cysteine residue;

(12) the fluorescent probe for super-resolution imaging according to any one of the above-described (1) to (10), wherein the compound containing the —SH group is glutathione; and

(13) The fluorescent probe for super-resolution imaging according to the above-described (1), wherein the compound represented by formula (I) is selected from the following group.

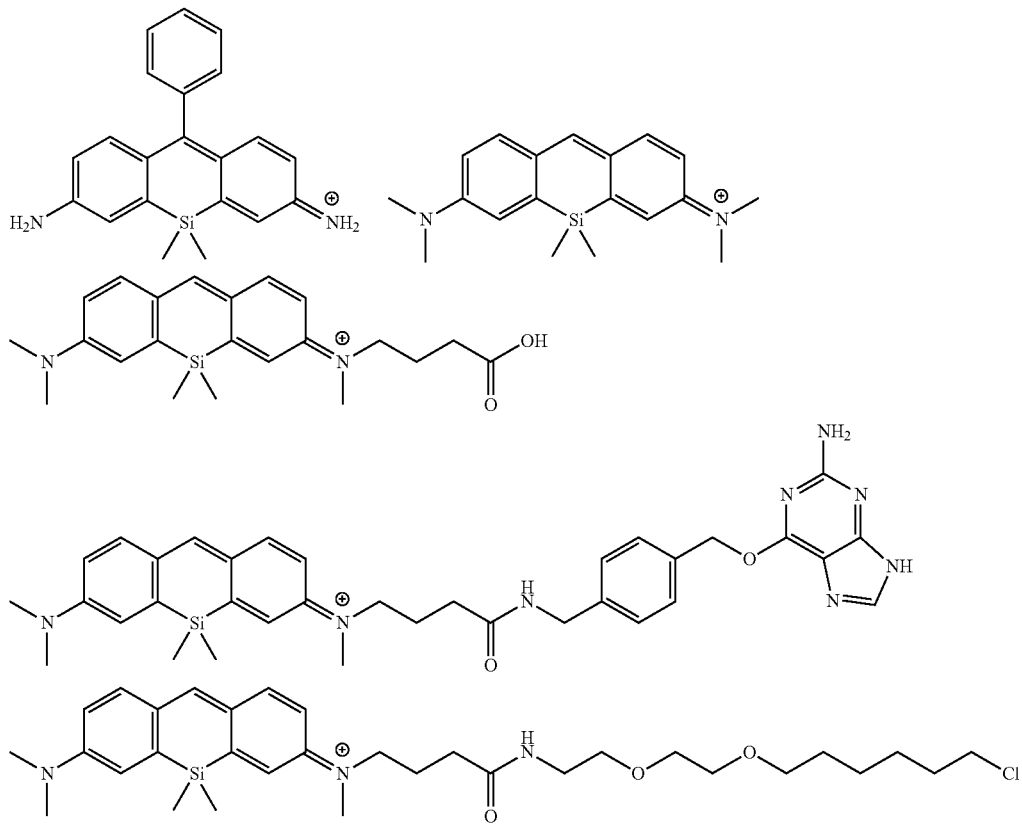

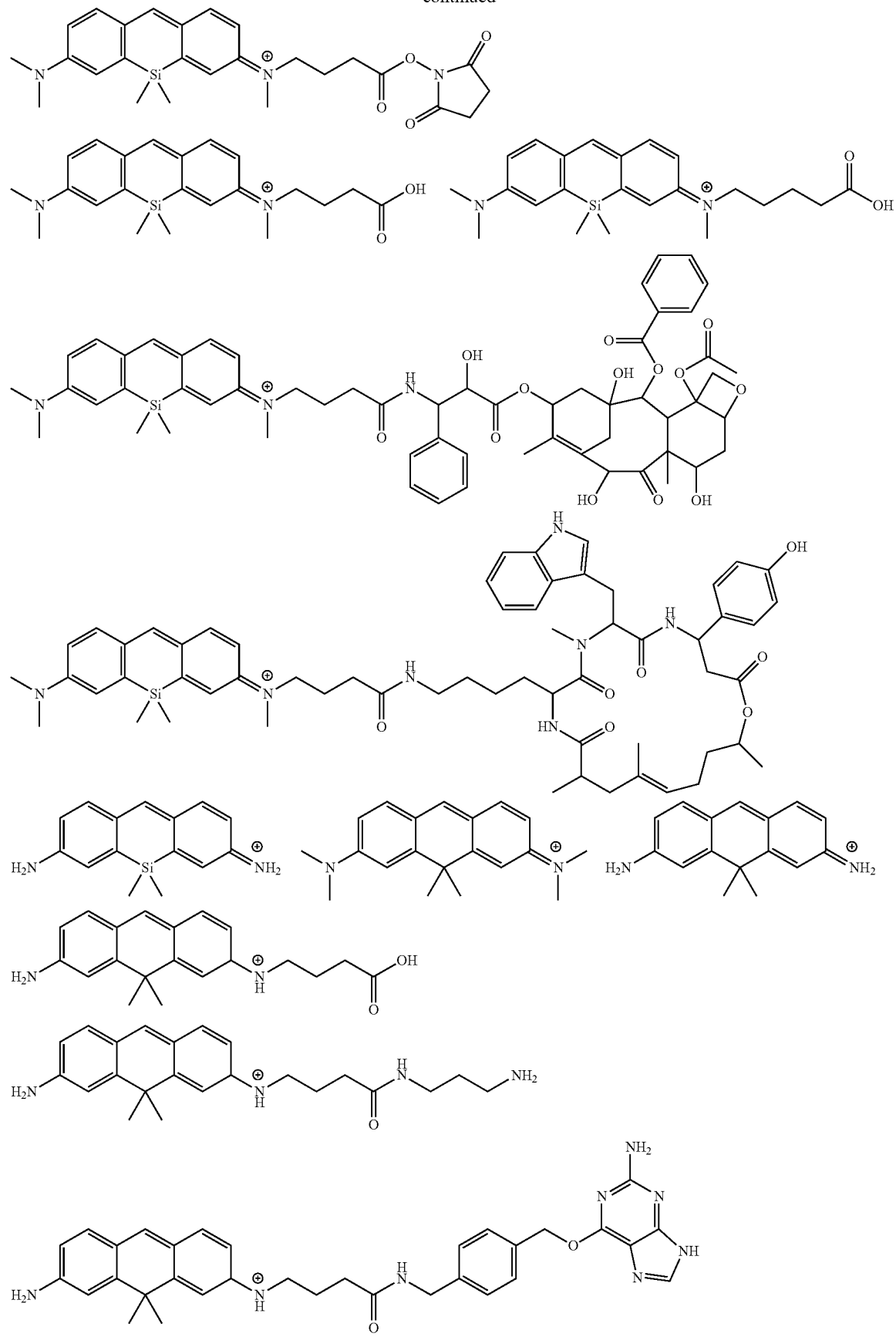

-continued

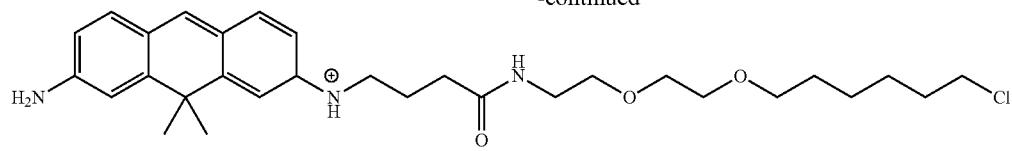

Another aspect of the present invention provides a super-resolution fluorescent imaging method using the fluorescent probe for super-resolution imaging according any one of the above-described (1) to (13), the method comprising bonding a probe molecule to a biomolecule, irradiating laser light in the presence of a compound containing a —SH group to acquire image data that has captured fluorescent light emission from the probe molecule, and analyzing and thereafter superimposing a plurality of the image data obtained by repeating the foregoing at a constant time interval to thereby obtain a super-resolution image of a structure of the biomolecule.

Advantages

The present invention uses an intermolecular equilibrium reaction between a probe molecule and glutathione or other intracellular substance as a principal of stochastic fluorescent light emission, and therefore high-concentration thiol is not required to be separately added as in conventional methods, laser irradiation required to place a fluorescent probe in a non-fluorescent state prior to data acquisition can be omitted, and the present invention can be used under conditions where laser intensity is reduced to about 1/10 that of conventional laser intensity, and cell toxicity can be reduced. Further, combining the fluorescent probe compound of the present invention also makes it possible to provide a technique for super-resolution imaging in multiple colors allowing observation in the same field of view.

Furthermore, the super-resolution fluorescence imaging probe of the present invention is suitable for labeling a target protein or the like when there is a bonding site (carboxyl group or the like) to a protein and the like in the molecule, and can be expected to be available for use in a wide range of research into not only fixed cells, but also into living cell lines. Also, a super-resolution fluorescence imaging method based on the probe is capable of using a commercially available microscope as an optical system, and is considered to be a highly versatile method. In this manner, utility value and economic effects for basic research of a developed probe and for the industry can be said to be very substantial.

BRIEF DESCRIPTION OF THE DRAWINGS

FIG. 8b illustrates a cross-sectional profile of normalized fluorescence intensity in a band-like region in the upper figure (scale bar: 3 μm) of the averaged images of FIG. 8a, and a cross-sectional profile of normalized recognized bright points in a band-like region in the upper figure (scale bar: 3 μm) of the super-resolution images. FIG. 8c illustrates a cross-sectional profile of normalized fluorescence intensity in a framed region in the lower figure (scale bar: 1 μm) of the averaged images of FIG. 8a, and a cross-sectional profile of normalized recognized bright points in the framed region in the lower figure (scale bar: 1 μm) of the super-resolution images. FIG. 8d illustrates a frequency distribution of positioning precision in relation to the bright points comprising the upper figure of the super-resolution images of FIG. 8a.

BEST MODE FOR CARRYING OUT THE INVENTION

Figure 1:
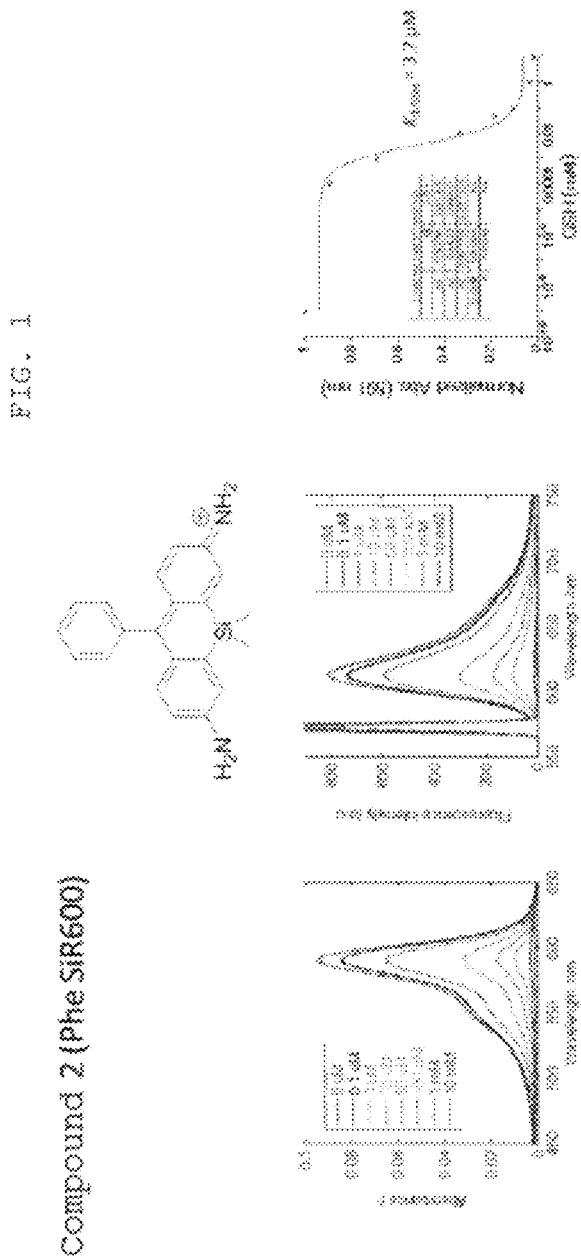
FIG. 1 illustrates an absorption spectrum change (left), a fluorescence spectrum change (center), and a plot of glutathione concentration dependency of absorbance (right) in each glutathione concentration of a compound 2, where the compound 2 is the super-resolution fluorescent imaging probe of the present invention.
Figure 2:
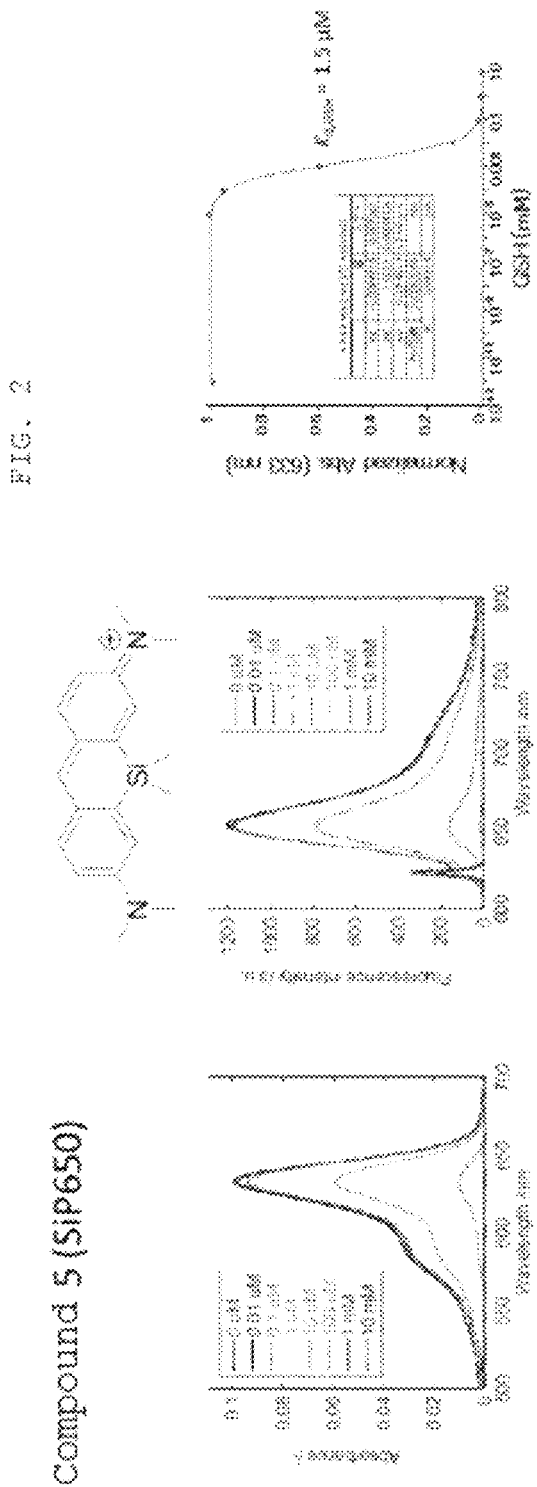
FIG. 2 illustrates the absorption spectrum change (left), the fluorescence spectrum change (center), and a plot of the glutathione concentration dependency of the absorbance (right) in each glutathione concentration of a compound 5, where the compound 5 is the super-resolution fluorescent imaging probe of the present invention.
Figure 3:
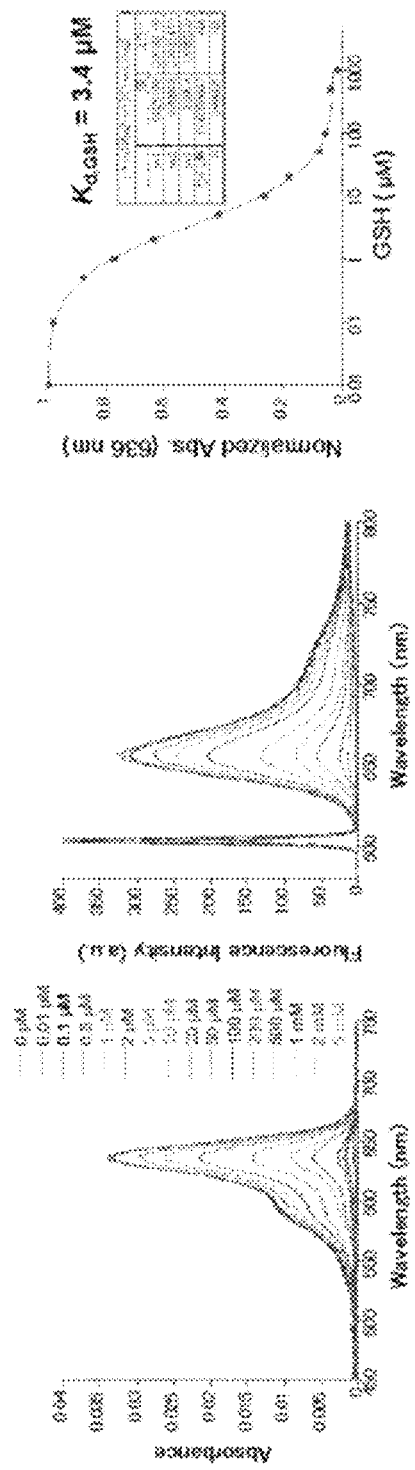
FIG. 3 illustrates the absorption spectrum change (left), the fluorescence spectrum change (center), and a plot of the glutathione concentration dependency of the absorbance (right) in each glutathione concentration of a compound 12, where the compound 12 is the super-resolution fluorescent imaging probe of the present invention.
Figure 4:
FIG. 4 illustrates the absorption spectrum change (left), the fluorescence spectrum change (center), and a plot of the glutathione concentration dependency of the absorbance (right) in each glutathione concentration of a compound 14, where the compound 14 is the super-resolution fluorescent imaging probe of the present invention.
Figure 4:
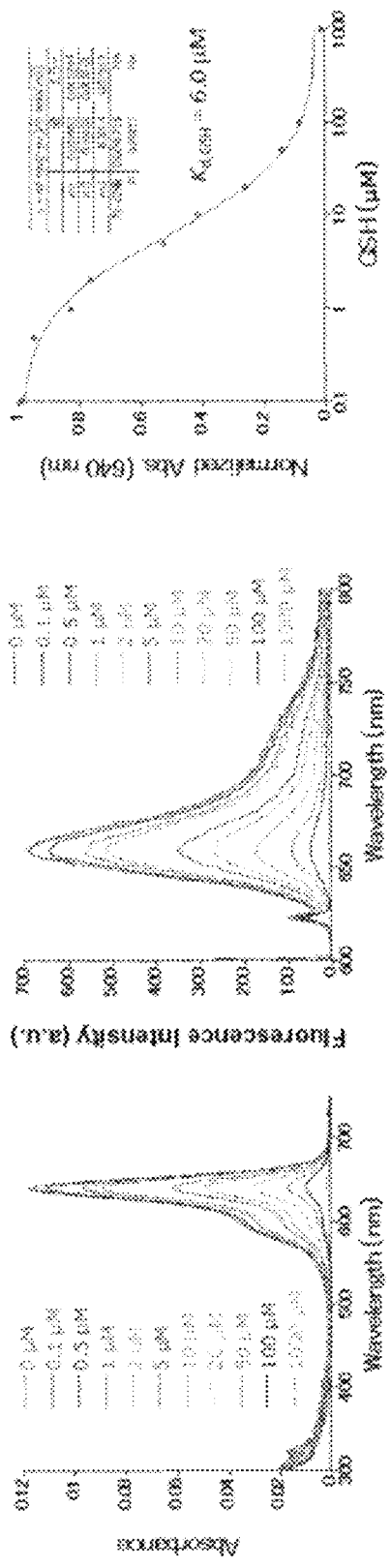
Figure 5:
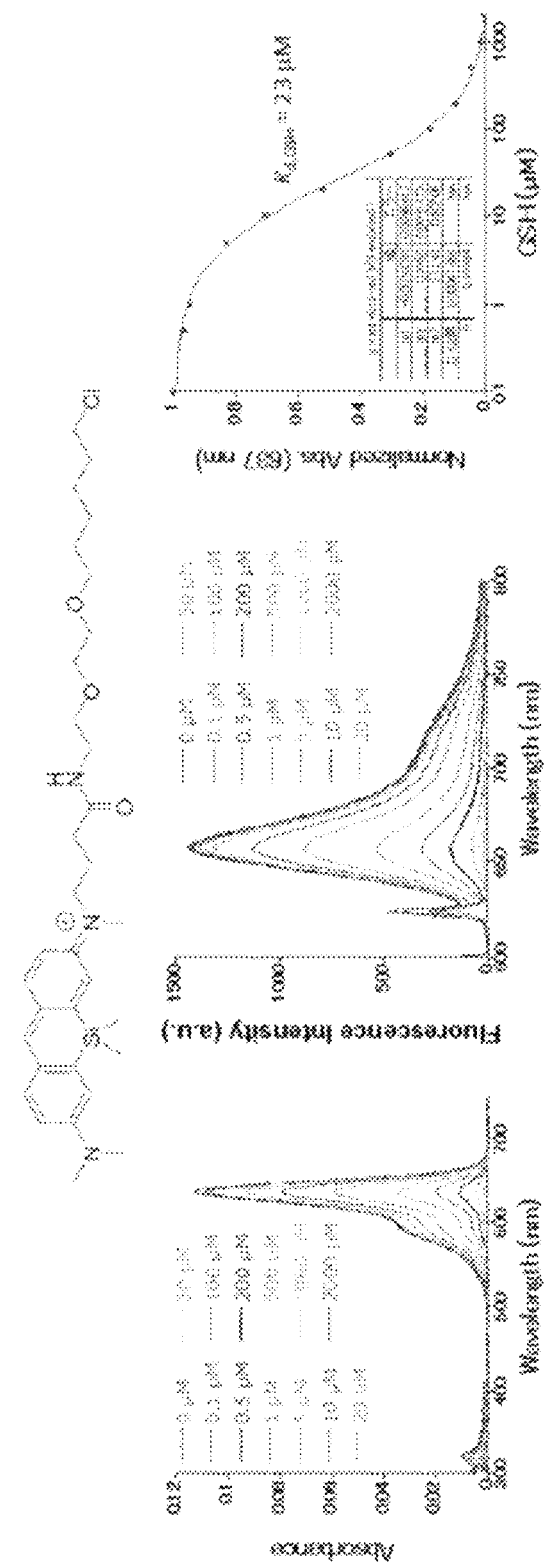
FIG. 5 illustrates the absorption spectrum change (left), the fluorescence spectrum change (center), and a plot of the glutathione concentration dependency of the absorbance (right) in each glutathione concentration of a compound 16, where the compound 16 is the super-resolution fluorescent imaging probe of the present invention.

Embodiments of the present invention are described below. The scope of the present invention is not limited by the following description, and the present invention may be modified, as appropriate, and implemented using configurations other than those given below as examples within the spirit of the invention.

1. Definitions

In the present specification, "halogen atom" refers to a fluorine atom, a chlorine atom, a bromine atom, or an iodine atom.

In the present specification, an "alkyl" may be any aliphatic hydrocarbon group that is linear, branched, cyclic, or comprising combinations thereof. A number of carbon atoms in the alkyl group is not particularly limited, and examples include 1 to 20 carbon atoms ($C_{1-20}$), 3 to 15 carbon ($C_{3-15}$), and 5 to 10 carbon atoms ($C_{5-10}$). When the number of carbon atoms is specified, this indicates an "alkyl" having a number of carbon atoms in the range of the number. For example, a $C_{1-8}$ alkyl includes methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. In the present specification, the alkyl group may have one or more arbitrary substituents. Examples of the substituent can include an alkoxy group, a halogen atom, an amino group, mono- or di-substituted amino group, a substituted silyl group, acyl, and the like, but these examples are not limiting. When the alkyl group has two or more substituents, they may be identical or different. The same applies to an alkyl moiety of other substituents containing an alkyl moiety (e.g., an alkoxy group (*1), an arylalkyl group, and the like).

In the present specification, when a certain functional group is defined as "optionally substituted," a type of substituent, a substitution position, and a number of substituents are not particularly limited, and when there are two or more substituents, they may be identical or different. Examples of the substituent can include an alkyl group, an alkoxy group, a hydroxyl group, a carboxyl group, a halogen atom, a sulfo group, an amino group, an alkoxycarbonyl group, an oxo group, and the like, but these examples are not limiting. Further substituents may be present on these substituents. Examples of such cases can include a halogenated alkyl group, a dialkyl amino group, and the like, but these examples are not limiting.

In the present specification, an "aryl" may be either a monocyclic or fused polycyclic aromatic hydrocarbon group, or may be an aromatic heterocyclic ring containing one or more hetero atoms (e.g., an oxygen atom, a nitrogen atom, or a sulfur atom, etc.) as a ring-constituting atom. In such case, this may be referred to as "heteroaryl" or "heteroaromatic." Even when the aryl is either a monocyclic or fused ring, it may bond in all possible positions. Non-limiting examples of a monocyclic aryl include a phenyl group (Ph), thienyl group (2- or 3-thienyl group), pyridyl group, furyl group, thiazolyl group, oxazolyl group, pyrazolyl group, 2-pyrazinyl group, pyrimidinyl group, pyrrolyl group, imidazolyl group, pyridazinyl group, 3-isothiazolyl group, 3-isoxazolyl group, and 1,2,4-oxadiazol-5-yl group, 1,2,4-oxadiazole-3-yl group, or the like. Non-limiting examples of a fused polycyclic aryl include 1-naphthyl group, 2-naphthyl group, 1-indenyl group, 2-indenyl group, 2,3-dihydroinden-1-yl group, 2,3-dihydroinden-2-yl group, 2-anthryl group, indazolyl group, quinolyl group, isoquinolyl group, 1,2-dihydroisoquinolyl group, 1,2,3,4-tetrahydroisoquinolyl group, indolyl group, isoindolyl group, phthalazinyl group, quinoxalinyl group, benzofuranyl group, 2,3-dihydrobenzofuran-1-yl group, 2,3-dihydrobenzofuran-2-yl group, 2,3-dihydrobenzothiophene-1-yl group, 2,3-dihydrobenzothiophene-2-yl group, benzothiazolyl group, benzimidazolyl group, fluorenyl group, thioxanthenyl group, or the like. In the present specification, the aryl group may have one or more arbitrary substituents on the ring. Examples of the substituent can include an alkoxy group, halogen atom, amino group, mono- or di-substituted amino group substituted silyl group, acyl, or the like, but these examples are not limiting. When the aryl group has two or more substituents, they may be identical or different. The same applies to an aryl moiety of other substituents containing an aryl moiety (e.g., an aryloxy group, an arylalkyl group, or the like).

In the present specification, an "alkoxy group" is a structure in which the alkyl group is bonded to an oxygen atom and includes, e.g., a saturated alkoxy group that is linear, branched, cyclic, or a combination thereof. Preferred examples include a methoxy group, ethoxy group, n-propoxy group, isopropoxy group, cyclopropoxy group, n-butoxy group, isobutoxy group, s-butoxy group, t-butoxy group, cyclobutoxy group, cyclopropylmethoxy group, n-pentyloxy group, cyclopentyloxy group, cyclopropylethyloxy group, cyclobutylmethyloxy group, n-hexyloxy group, cyclohexyloxy group, cyclopropyl propyloxy group, cyclobutylethyloxy group, cyclopentylmethyloxy group, or the like.

"Amide" as used in the present specification includes both RNR'CO— (in the case of R=alkyl, arylaminocarbonyl-) and RCONR'— (in the case of R=alkyl, alkylcarbonyl amino-).

"Ester" as used in the present specification includes both ROCO— (alkoxycarbonyl-, when R=alkyl) and RCOO— (alkylcarbonyloxy-, when R=alkyl).

In the present specification, the term "ring structure" refers to a heterocyclic or carbocyclic group when formed by a combination of two substituents, and such groups may be saturated, unsaturated, or aromatic. Therefore, cycloalkyl, cycloalkenyl, aryl, and heteroaryl as defined above are included. Examples include cycloalkyl, phenyl, naphthyl, morpholinyl, piperidinyl, imidazolyl, pyrrolidinyl, pyridyl, and the like. In the present specification, substituents may form another substituent and ring structure, and when such substituents are bonded to each other, a person skilled in the art could understand that a bond to a specific substitution, e.g., hydrogen, is formed. Therefore, when it is described that particular substituents together form a ring structure, a person skilled in the art could understand that the ring structures can be formed by conventional chemical reactions and are readily generated. Any such ring structures and formation processes thereof are within the purview of a person skilled in the art.

2. Fluorescent Probe for Super-Resolution Imaging

A first aspect of the fluorescent probe for super-resolution imaging of the present invention comprises a compound having a structure represented by the following general formula (I).

(I)

[Chemical formula 2]

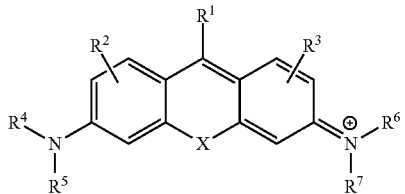

In general formula (I) noted above, X represents an oxygen atom, $C(R^a)(R^b)$, or $Si(R^a)(R^b)$. The excitation wavelength is shifted by substitution of X, and therefore an excitable multicolor-imaging probe can be provided by a generic laser. Here, $R^a$ and $R^b$ each independently represent a hydrogen atom or an alkyl group. When $R^a$ and $R^b$ are alkyl groups, they may have one or more substituent groups, and examples of such substituent groups may have one or two or more of an alkyl group, an alkoxy group, a halogen atom, a hydroxyl group, a carboxyl group, an amino group, a sulfo group, and the like. $R^a$ and $R^b$ are preferably both a methyl group. In some cases, $R^a$ and $R^b$ may be bonded to each other to form a ring structure. For example, when $R^a$ and $R^b$ are both alkyl groups, $R^a$ and $R^b$ may be bonded to each other to form a spiro ring. The formed ring is preferably, e.g., a ring of about 5 to 8 members.

$R^1$ represents a hydrogen atom or an optionally substituted aryl. Examples of the substituent in the optionally substituted aryl include an alkyl group, an alkoxy group, a halogen atom, a hydroxyl group, a carboxyl group, an amino group, a sulfo group, and the like, but these examples are not limiting. Also, there may be one or two or more substituents. Preferably, $R^1$ is a hydrogen atom or an optionally substituted phenyl group. However, when $R^1$ is a phenyl group, position 2 or position 6 of the benzene ring of the phenyl group (i.e., a position where $R^1$ is in the ortho position in relation to a xanthene ring moiety serving as a substituent on the benzene ring) preferably has no substituent from a viewpoint of reactivity with a nucleophilic compound. When $R^1$ is a hydrogen atom, the compound of general formula (I) has a structure similar to pyronine, and when $R^1$ is phenyl, the compound of general formula (I) has a structure similar to rosamine.

$R^2$ and $R^3$ each independently represent one to three identical or differing substituents that are independently selected from a group consisting of a hydrogen atom, a hydroxyl group, a halogen atom, an optionally substituted alkyl group, an optionally substituted sulfo group, an optionally substituted carboxyl group, an optionally substituted ester group, an optionally substituted amide group and an optionally substituted azide group. Preferably, $R^2$ and $R^5$ are both hydrogen atoms. In some cases, one of $R^2$ and $R^3$ may also include a labeled substituent capable of covalently bonding to a later-described protein or other biomolecule. In such a case, $R^2$ and $R^3$ may themselves be a labeled substituent, or are optionally substituted with a substituent containing a labeled substituent.

$R^4$ and $R^5$ each independently represent a hydrogen atom or an alkyl group, or $N(R^4)(R^5)$ may form an amide group or a carbamate group. When $R^4$ and $R^5$ both represent an alkyl group, they may be identical or different. For example, $R^4$ and $R^5$ are preferably each independently a hydrogen atom, a methyl group, or an ethyl group from a viewpoint of a nucleophilic addition reaction rate with the nucleophilic compound containing a —SH group, and a case is further preferred where $R^4$ and $R^5$ are both hydrogen atoms, or are both a methyl group. One of $R^4$ and $R^5$ is preferably a hydrogen atom and the other a carbonyl group. In this case, $N(R^4)(R^5)$ forms an amide bond. The other substituent bonded with the carbonyl group is not particularly limited, but an alkyl group is preferred, and a methyl group is more preferred. In some cases, $N(R^4)(R^5)$ preferably contains a substituent (labeled substituent) capable of bonding covalently, non-covalently, or otherwise with a protein or other biomolecule. In such a case, they themselves may be a labeling substituent, or are optionally substituted with a substituent containing a labeling substituent. For example, either or both of $R^4$ and $R^5$ are optionally substituted with a substituent containing a ligand used in HaloTag (registered trademark), a benzylguanino derivative, which is a substrate for SNAP-Tag, and/or N-hydroxysuccinimide or other leaving group. Alternatively, they are optionally substituted with a substituent containing phalloidin or other cyclic peptide binding to paclitaxel and docetaxel and other taxanes and actin filaments that bind to microtubules. Alternatively, they are optionally substituted with N-hydroxysuccinimide, the N-hydroxysuccinimide forming a bond with an amino group of, for example, a lysine residue of protein present in a cell membrane. Furthermore, they are optionally substituted with an azide group that forms a covalent bond by click chemistry with an alkyne structure introduced to protein, by bonding or the like with an amino group via N-hydroxysuccinimide. Such a labeling substituent is not particularly limited and those known in the technical field may be used.

When $R^4$ or $R^5$ is an alkyl group, each may be used together with $R^2$ to form a ring structure containing a nitrogen atom that bonds therewith. In such a case, only one combination of $R^4$ and $R^2$, or $R^3$ and $R^2$ may form a ring structure, or both may form a ring structure.

$R^6$ and $R^7$ can each independently represent a hydrogen atom or an alkyl group, or $N(R^4)(R^7)$ can form an amide group or a carbamate group. When $R^4$ or $R^7$ both represent an alkyl group, they may be identical or different. For example, preferably, $R^6$ and $R^7$ are each independently a hydrogen atom, a methyl group, or an ethyl group, and the case in which both $R^4$ and $R^7$ are hydrogen atoms or both are a methyl group is more preferred. One of $R^6$ or $R^7$ is preferably a hydrogen atom and the other a carbonyl group. In this case, $N(R^6)(R^7)$ forms an amide bond. The other substituent bonded to the carbonyl group is not particularly limited, but an alkyl group is preferred, and a methyl group is more preferred. In some cases, $N(R^6)(R^7)$ preferably contains the above-described labeling substituent. In such a case, they themselves may be a labeling substituent, or are optionally substituted with a substituent containing a labeling substituent. As described above, such a labeling substituent is not particularly limited and those known in the technical field may be used.

Also, when $R^6$ or $R^7$ is an alkyl group, each may be used together with $R^3$ to form a ring structure containing a nitrogen atom that bonds therewith. In such a case, only one combination of $R^6$ and $R^3$, or $R^7$ and $R^3$ may form a ring structure or both may form a ring structure.

Examples of preferred combinations of each of the above substituents include X being $C(R^a)(R^b)$ or being $Si(R^a)(R^b)$, $R^a$ and $R^b$ each being a methyl group, $R^1$ being a hydrogen atom or a phenyl group, $R^2$ and $R^3$ each being a hydrogen atom, and $R^4$, $R^5$, $R^6$, and $R^7$ each being a hydrogen atom or each being a methyl group. Similarly, preferable cases are: X being an oxygen atom $R^1$ being a hydrogen atom or a phenyl group, $R^2$ and $R^3$ each being a hydrogen atom, and $R^4$, $R^5$, $R^6$, and $R^7$ each being a hydrogen atom or each being a methyl group.

Specific examples of representative compounds of formula (I) as the super-resolution fluorescence imaging probe of the present invention can include:

[Chemical formula 3]

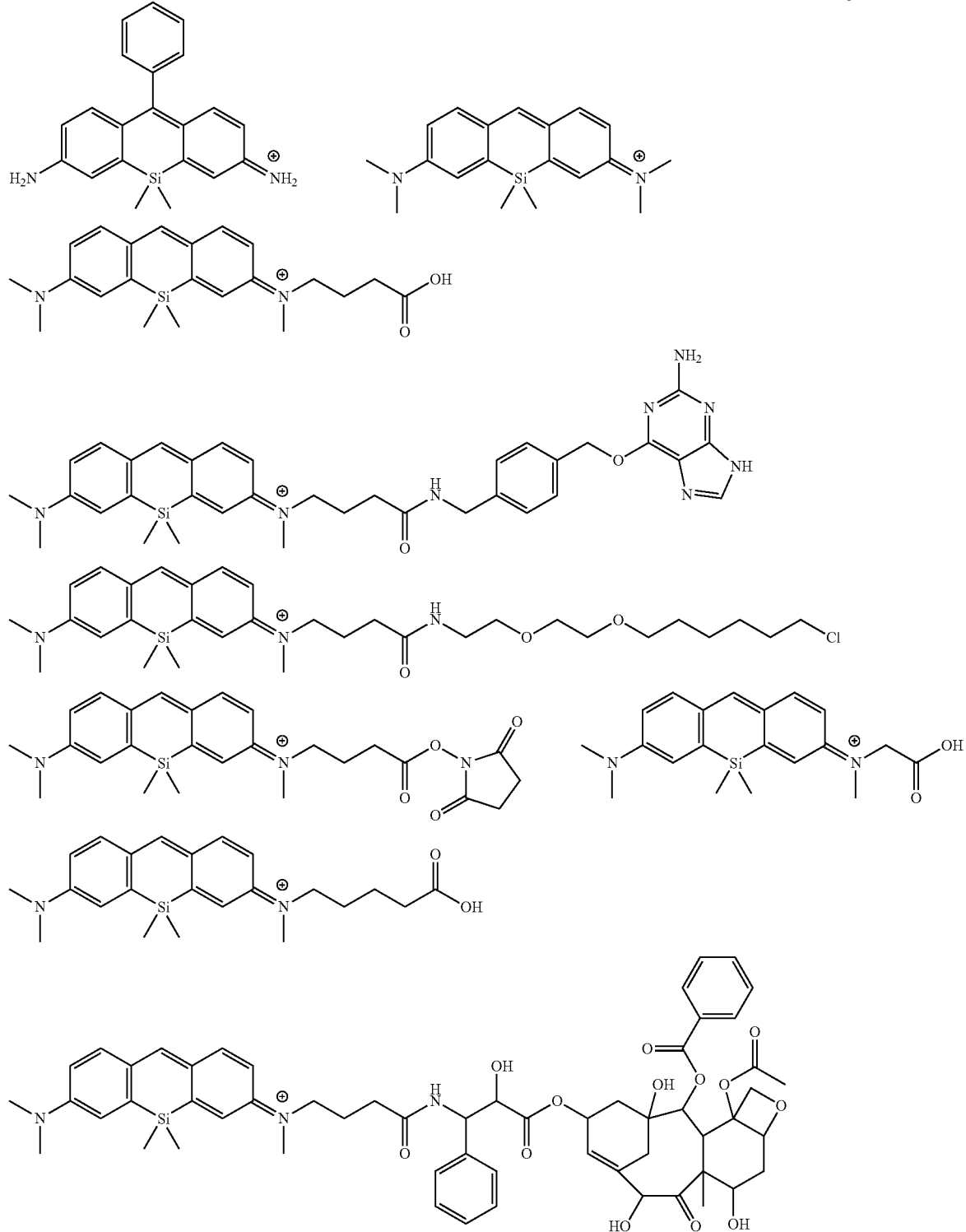

-continued

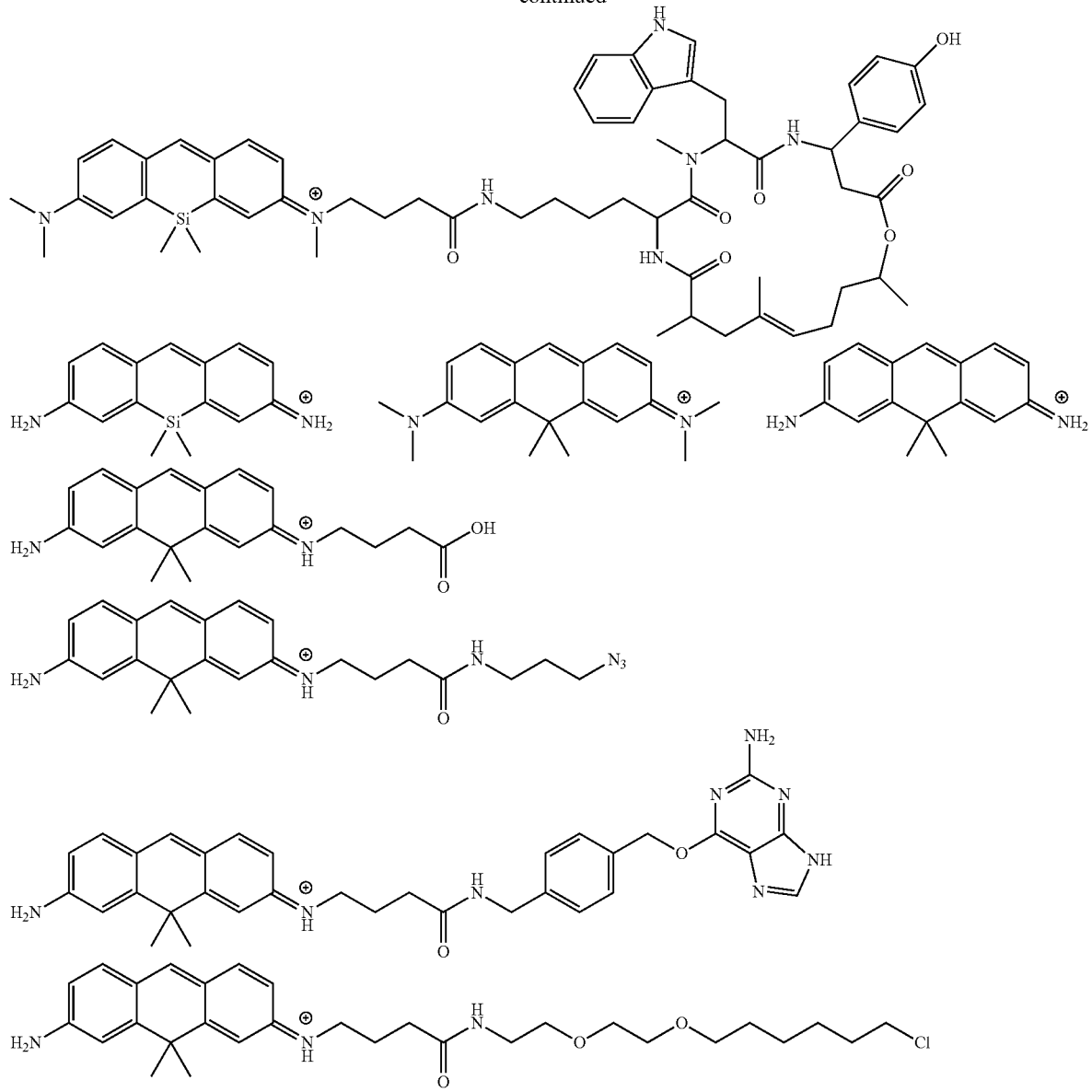

However, no limitation is imposed thereby. Also, the compounds may have a labeling substituent group in any position.

The compound represented by the formula (I) has a monovalent positive charge at the N atom to which $R^6$ and $R^7$ connect, and is therefore ordinarily present as a salt. Such salts can include base addition salts, acid addition salts, amino acid salts, and the like. Examples of base addition salts can include sodium salt, potassium salt, calcium salt, magnesium salt and other metal salts, ammonium salt, or triethylamine salt, piperidine salt, morpholine salt, and other organic amine salts. Examples of acid addition salts can include hydrochloride, sulfate, nitrate, and other mineral acid salts, trifluoroacetic acid salt and other carboxylates, methanesulfonate, p-toluenesulfonate, citrate, oxalate, and other organic acid salts. An example of the amino acid salt can be glycine salt or the like. Naturally, no limitation is imposed by these salts.

Compounds represented by the formula (I) may have one or two or more asymmetric carbons depending on the type of substituent group, and optical isomers, or diastereoisomers and other stereoisomers may be present. Stereoisomers in pure form, any mixture of stereoisomers, racemates, and the like each fall within the scope of the present invention.

The compound represented by the formula (I) or a salt thereof may be present as a hydrate or solvate, and any of these substances fall within the scope of the present invention. The type of a solvent that forms the solvate is not particularly limited, and examples can include ethanol, acetone, isopropanol, and other solvents.

The fluorescent probe may be used as a composition by mixing an additive for use in physiological environments as necessary. Solubilizing agents, pH-adjusting agents, buffering agents, isotonizing agents, and other additives may be used 33 such an additive, and the amount of these formulations can be selected, as appropriate, by a person skilled in the art. These compositions may be provided as a mixture in powder form, a freeze-dried product, granules, tablets, liquids, or other compositions in a suitable form.

In the examples of the present specification, a production process for representative compounds included in the compounds of the present invention represented by the formula (I) is specifically indicated, and therefore, a person skilled in the art can readily produce any compound included in formula (I) by referring to the disclosure of the present specification and by selecting, as appropriate, the starting material and/or reagents, the reaction conditions, and the like as necessary.

3. Super-Resolution Fluorescence Imaging Method Using the Probe of the Present Invention The super-resolution fluorescence imaging method of the invention comprises bringing a probe molecule of formula (I) described above into contact with a biomolecule, irradiating laser light in the presence of a compound containing a —SH group to acquire image data by CCD camera or the like in which fluorescent light emission from the probe molecule has been captured, and analyzing and thereafter superimposing a plurality of the image data obtained by repeating the foregoing at a constant time interval to thereby obtain a super-resolution image of the structure of the biomolecule. Examples of the biomolocule to be observed include a cell membrane (lipid), protein, DNA, RNA, and the like.

Super-resolution fluorescence imaging by single-molecule localization microscopy (SMLM) typically can be used as the imaging method, and the principles thereof are described in detail in Non-Patent Reference 1. Therefore, the basic procedure in the super-resolution fluorescence imaging method of the present invention can be obtained by referring to the super-resolution fluorescence imaging technique described in said reference, except for the use of the probe of formula (I).

The super-resolution fluorescence imaging method of the present invention uses, as a light-flickering mechanism, a phenomenon in which the compound of formula (I) in an aqueous solution loses absorption and fluorescence in the visible region upon receiving a nucleophilic addition of glutathione or other —SH group-containing compound, and regains absorption and fluorescence when the added —SH group-containing compound dissociates. The mechanism of this nucleophilic addition-dissociation equilibrium reaction is given below.

[Chemical formula 4]

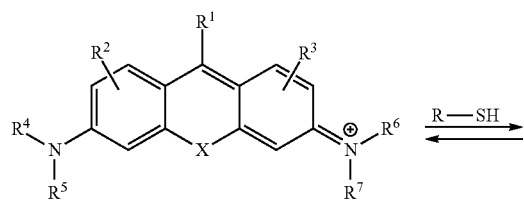

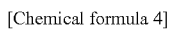

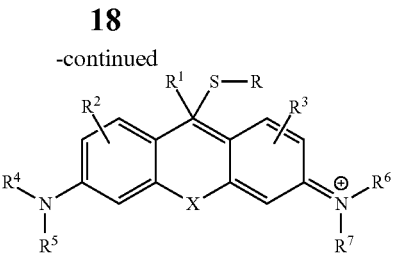

Fluorescent quenching/colorless

Pre-reaction (left side) compound (I) absorbs excitation light of about 400 to 700 nm and emits strong fluorescence, whereas compound (II) loses absorption and fluorescence in the visible light region when position 9 of a xanthene-like fused ring undergoes nucleophilic attack by a nucleophilic compound (in this case, "R—SH" represents the compound containing glutathione or other —SH group). The nucleophilic addition reaction between molecules is a reversible nucleophilic addition-dissociation equilibrium reaction, and therefore, use is made of the fact that fluorescent flickering suitable for super-resolution fluorescent imaging is obtained by using a probe molecule having a predetermined dissociation constant and nucleophilic addition reaction rate. In addition to —SH group-containing compounds given herein, compounds containing —OH groups such as hydroxide ions and water, or —NH group-containing compounds such as lysine residue in protein, for example, can be used as nucleophilic compounds that bring about the nucleophilic addition-dissociation equilibrium reaction.

In particular, glutathione is known to be present in cells in a concentration of an order around several millimolars, and therefore, super-resolution fluorescent imaging can be carried out in living cells under physiological conditions by optimizing the frame rate of a CCD camera or the like, which is a detector in which advantageous fluorescent flickering induced by the equilibrium reaction is generally used in the presence of glutathione in the noted concentration range, without the use of a separately added high-concentration thiol or reducing agent, and/or high-intensity laser irradiation, or other external stimuli in order to bring about a non-fluorescent state of the probe molecule, as in the conventional art.

Furthermore, the present invention is advantageous in that the intensity of the used laser can be about 1/10 that of the conventional level, and it is therefore possible to reduce cell toxicity. The intensity of the laser is preferably about 0.0001 to 10 $kW/cm^2$, and is more preferably about 0.01 to 0.5 $kW/cm^2$ from a viewpoint of signal-to-noise ratio (S/N ratio), cell toxicity, and the like.

In super-resolution fluorescence imaging by SMLM, it is not preferred for the fluorescent probe molecules to emit light in locations closer together than the diffraction limit of light, and therefore, a probe molecule in a state of fluorescence emission in a single measurement must be at a constant percentage or less. Accordingly, an abundance ratio of compound (I) and compound (II) in the equilibrium is preferably 1:10000 to 1:10, and more preferably 1:1000 to 1:100 at room temperature in an aqueous solution of neutral conditions. In the particular case that the nucleophilic compound for carrying out a nucleophilic addition-dissociation equilibrium reaction with the probe molecule is glutathione, which is present in cells in a concentration of an order around several millimolars, in order to have such an abundance ratio, a dissociation constant $K_d$ of the nucleophilic addition-dissociation equilibrium reaction is preferably in a range of 0.1 μM to 10 mM and, from a viewpoint of improvement of labeling density, is more preferably in a range of 0.1 to 100 μM. The dissociation constant is expressed by $K_d$=[concentration of (I) in an equilibrium state][concentration of glutathione]/[concentration of (II) in the equilibrium state], and can be experimentally calculated using techniques well known in the technical field.

Also, in order to obtain a correspondence to the frame rate of the CCD camera or the like as the detector, service life of the compound of formula (I) in a fluorescent state is preferably in a range of 1 microsecond to 1 second and, from a viewpoint of improvement of the signal-to-noise ratio (S/N ratio), is more preferably in a range of 1 millisecond to 1 second. In order have such a service life range, a nucleophilic addition reaction rate constant in the equilibrium is preferably in a range of 1 to $1.0\times10^6$ s$^{-1}$, and more preferably in a range of 1 to 1000 s$^{-1}$ at room temperature in an aqueous solution of neutral conditions. The reaction rate can be calculated by using laser flash photolysis or other system known in the technical field in order to excite the fluorescent probe using a nanosecond laser, and measuring transient absorption on an order of nanoseconds to milliseconds.

A compound that functions as a nucleophilic molecule in a nucleophilic addition-dissociation equilibrium reaction is a compound containing a —SH group, and is preferably glutathione which is a nucleophilic molecule present in the cell. However there is no limitation to glutathione as giver, here, and as long as it is a molecule having a —SH group in the molecule, the nucleophilic molecule may broadly comprise a peptide and/or a compound having a cysteine residue, and these compounds or the like can also be used in the present invention so long as the equilibrium reaction is obtained. Further, as described above, in lieu of the compound containing an —SH group, a compound having a nucleophilic functional group such as a —OH group or a —NH group in the molecule, e.g., a compound having water, a lysine residue, or the like, or a peptide can be included, and can be used as a nucleophilic compound in the present invention as long as the equilibrium reaction can be obtained.

As described above, the dissociation constant and nucleophilic addition reaction rate constant can be obtained by molecular design in which an appropriate combination is selected as substituents or the like in compounds of formula (I) to obtain a more optimal dissociation constant and reaction rate.

EXAMPLES

The present invention is described in greater detail below using examples, but the present invention is not limited thereby.

Example 1

1. Synthesis of Probe Molecule

As described below, compounds 2, 5, 12, 14, 16, 17, 28, 32, 33, 34, and 35, which are super-resolution fluorescence imaging probes of the present invention, were each synthesized.

[Synthesis of Compound 2]

Compound 2 was synthesized in accordance with the following scheme. Compound 1 is disclosed in Kushida, K. et al. Bioorg. Med. Chem. Lett. 22 (2012) 3508-3911, and synthesis was conducted on the basis thereof.

[Chemical formula 5]

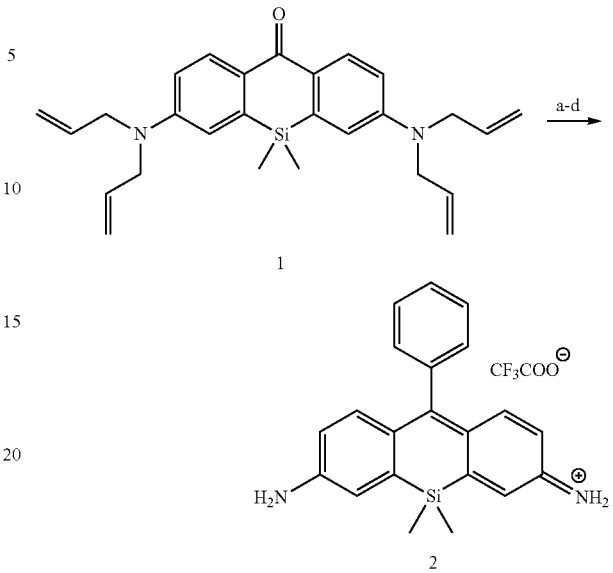

a) i) PhLi, THF, -78° C., ii) 1N HClaq., b) NaBH$_4$, MeOH, c) 1,3-dimethylbarbituric acid, Pd(PPh$_3$)$_4$, CH$_2$Cl$_2$, d) p-chloranil. CH$_2$Cl$_2$.

Compound 1 (23.8 mg, 0.056 mmol, 1 eq.) was dissolved in THF (5 mL) and stirred at -78° C. under an argon atmosphere. A 1.9-M phenyl lithium dibutyl ether solution (200 μL, 0.330 mmol, 7 eq.) was slowly added, and the mixture was stirred at room temperature for 1 hour. The mixture was acidified by addition of 1 N of hydrochloric acid, an aqueous solution of saturated sodium hydrogen carbonate was subsequently added, then extracted three times using dichloromethane, the resulting organic phase was washed using a saturated sodium chloride solution, dried using anhydrous sodium sulfate and filtered, and the solvent was thereafter removed under reduced pressure. The resulting compound was dissolved in methanol (2 mL), and sodium borohydride was added until the color of the solution became a light yellow color. Water was added to stop the reaction and extracted twice using dichloromethane, the resulting organic layer was washed using a saturated sodium chloride solution and dried using anhydrous sodium sulfate, and the solvent was removed under reduced pressure. The resulting compound was dissolved in deoxygenated dichloromethane (5 mL), 1,3-dimethylbarbituric acid (185 mg, 1.17 mmol, 21 eq.) and tetrakis (triphenylphosphine) palladium (11 mg, 9 μmol, 0.2 eq.) were added, and the mixture was stirred at room temperature overnight. The reaction liquid was extracted using ethyl acetate, washed twice using an aqueous solution of saturated sodium hydrogen carbonate and washed using a saturated sodium chloride solution, dried using anhydrous sodium sulfate and filtered, and the solvent was thereafter removed under reduced pressure. The resulting compound was stirred for 5 minutes at room temperature with an addition of chloranil (23 mg, 0.094 mmol, 1.7 eq.), the dark bluish purple reaction liquid was separated by silica gel column chromatography (eluent: dichloromethane/methanol=100/0 to 80/20), a bluish purple fraction was recovered, the solvent was distilled away under reduced pressure and was further purified by HPLC (eluent A (H$_2$O, 1% acetonitrile, 0.1% trifluoroacetic acid); eluent B (acetonitrile, 1% H$_2$O) (first round: A/B=90/10 to 10/90, 25 min.; second round: A/B=70/30 to 30/70, 25 min.)), and the objective compound 2 (10.2 mg, 41%) was obtained as a bluish purple solid.

[Synthesis of Compound 4]

Compound 4 was synthesized in accordance with the following scheme. Synthesis of compounds 3 and 4 is disclosed in Y. Koide et al. J. Am. Chem. Soc. 2012, 134, 5029-5031, and synthesis was conducted on the basis thereof.

[Chemical formula 6]

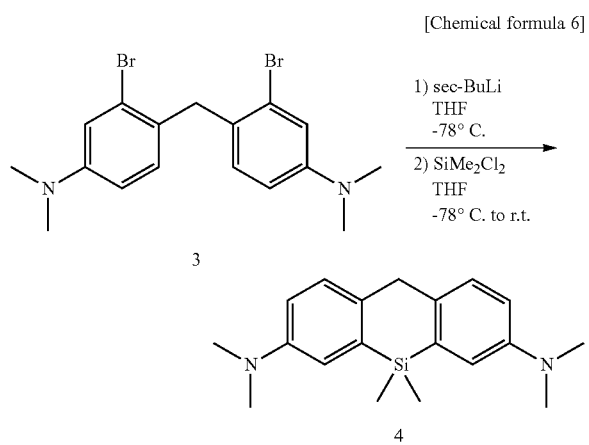

Compound 3 (1.80 g, 4.37 mmol, 1 eq.) was dissolved in THF (100 mL) and stirred at −78° C. for 15 minutes under an argon atmosphere. A 1.1-M sec-butyl lithium cyclohexane/n-hexane solution (9 mL, 9.9 mmol, 2.3 eq.) was slowly added over 15 minutes. Dichlorodimethylsilane (700 µL, 5.75 mmol, 1.3 eq.) was then diluted in THF (5 mL) and added, and the mixture was returned to room temperature gradually and stirred for 2 hours. The mixture was acidified by addition of 1 N of hydrochloric acid, a saturated aqueous sodium hydrogen carbonate solution was then added, and the THF removed under reduced pressure. The resulting aqueous layer was extracted using ethyl acetate, the organic phase was then washed using water and a saturated sodium chloride solution and dried using anhydrous sodium sulfate, and the solvent was removed under reduced pressure. The resulting residue was purified by medium-pressure silica gel chromatography (eluent: n-hexane/ethyl acetate=55/5 to 80/20), and the objective compound 4 (852 mg, 63%) was obtained as a light yellow solid.

$^1$H NMR (400 MHz, CDCl$_3$): δ 0.28 (s, 3H), 2.96 (s, 12H), 3.93 (s, 2H), 6.76 (dd, J=8.4, 2.8 Hz, 2H), 7.02 (d, J=2.8 Hz, 2H), 7.21 (d, J=8.4 Hz, 2H); $^{13}$C NMR (100 MHz, CDCl$_3$): δ −2.6, 39.3, 41.3, 114.2, 117.7, 128.6, 135.3, 136.2, 148.3.

[Synthesis of Compound 5]

Compound 5 was synthesized in accordance with the following scheme.

[Chemical formula 7]

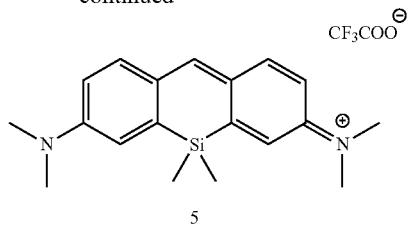

Compound 4 (36.5 mg, 0.115 mmol, 1 eq.) was added to chloranil (27 mg, 0.115 mmol, 1 eq.), stirred at room temperature for 10 minutes, a dark blue reaction solution was separated out by silica gel column chromatography (eluent: dichloromethane/methanol=100/0 to 80/20), a blue fraction was recovered, the solvent was distilled away under reduced pressure, further purification was carried out by HPLC (eluent A (H$_2$O, 1% acetonitrile, 0.1% trifluoroacetic acid), eluent B (acetonitrile, 1% H$_2$O) (A/B=90/10 to 10/90, 25 min)), and the objective compound 5 (53.6 mg, 96%) was obtained as a blue solid.

$^1$H NMR (400 MHz, CD$_3$CN): δ 0.50 (s, 6H), 3.30 (3, 12H), 6.89 (dd, J=9.2, 2.7 Hz, 2H), 7.25 (d, J=2.7 Hz, 2H), 7.64 (d, J=9.2 Hz, 2H), 7.80 (s, 1H); ARMS (ESI$^+$): Calcd for [M]$^+$, 309.17815, Found, 309.17801 (−0.1 mmu).

[Synthesis of compound 6]

Compound 6 was synthesized in accordance with the following scheme.

[Chemical formula 8]

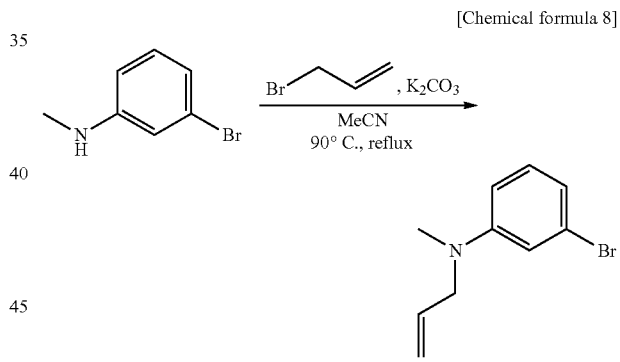

Potassium carbonate (7.46 g, 54.0 mmol, 2.0 eq.) was suspended in acetonitrile (20 mL), 3-bromo-N-methylaniline (4.96 g, 26.7 mmol, 1 eq.) and allyl bromide (3.87 g, 31.3 mmol, 1.2 eq.) were added, and the mixture was heated and refluxed overnight at 90° C. while being stirred. The reaction mixture was filtered through celite, the filtration residue and celite were then washed using ethyl acetate, and the solvent was removed under reduced pressure from a mixture of filtrate and washing solution. The resulting residue was purified by medium-pressure silica gel chromatography (eluent n-hexane/ethyl acetate=100/0 to 98/2) to obtain the objective compound 6 (5.98 g, 99%).

$^1$H NMR (400 MHz, CDCl$_3$): δ 2.95 (s, 3H), 3.91-3.93 (m, 2H), 5.15-5.21 (m, 2H), 5.79-5.89 (m, 1H), 6.63-6.65 (m, 1H), 6.82-6.86 (m, 2H), 7.06-7.10 (m, 1H); $^{13}$C NMR (100 MHz, CDCl$_3$): δ 38.1, 55.0, 110.9, 115.0, 116.4, 119.1, 123.5, 130.4, 133.1, 150.7; HRMS (ESI$^+$): Calcd for [M+H]$^+$, 226.02259, Found, 226.02210 (−0.5 mmu).

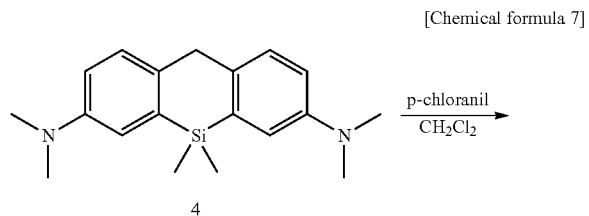

[Synthesis of Compound 7]

Compound 7 was synthesized in accordance with the following scheme.

[Chemical formula 9]

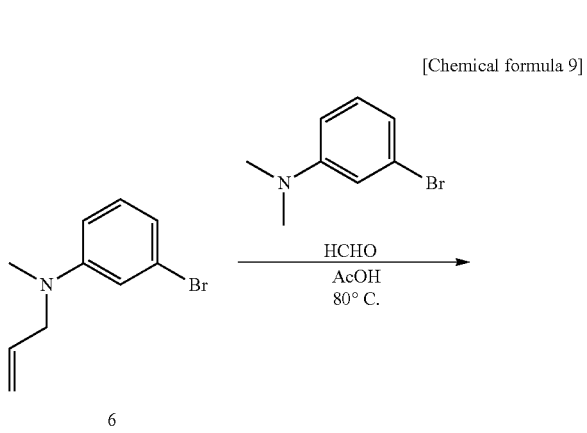

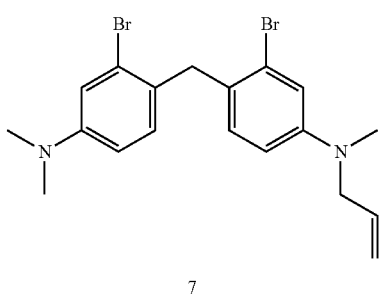

Compound 6 (4.60 g, 20.4 mmol, 1 eq.) and 3-bromo-N,N-dimethylaniline (5.00 g, 25.0 mmol, 1.2 eq.) were dissolved in acetic acid (10 mL), and 37% aqueous formaldehyde solution (6.30 mL, 227 mmol, 11 eq.) was added, allowed to gradually warm to 80° C., and thereafter heated for 3 hours. Acetic acid was removed from the reaction mixture under reduced pressure, a saturated aqueous sodium hydrogen carbonate solution was added and then extracted using dichloromethane, the organic phase was washed using water and a saturated sodium chloride solution and dried using anhydrous sodium sulfate, and the solvent was removed under reduced pressure. The resulting residue was purified by medium-pressure silica gel chromatography (eluent: n-hexane/dichloromethane=80/20 to 70/30 to 60/40 to 50/50) to obtain the objective compound 7.

$^1$H NMR (400 MHz, CDCl$_3$): δ 2.92 (s, 3H), 2.93 (s, 6H), 3.88-3.90 (m, 2H), 4.02 (s, 2H), 5.15-5.20 (m, 2H), 5.83 (ddt, 1H, J=14.8, 12.6, 4.9 Hz), 6.57-6.62 (m, 2H), 6.85 (d, 1H, J=8.6 Hz), 6.88 (d, 1H, J=8.6 Hz), 6.95 (d, 1H, J=2.7 Hz), 6.96 (d, 1H, J=2.6 Hz); $^{13}$C NMR (100 MHz, THF-d$_8$): δ 38.2, 40.5, 40.6, 55.7, 112.6, 112.7, 116.3, 116.7, 116.8, 126.16, 126.17, 127.6, 127.7, 131.5, 131.6, 134.7, 150.1, 151.2; HRMS (ESI$^+$): Calcd for [M+H]$^+$, 437.02225, Found, 437.02225 (±0.0 mmu).

[Synthesis of Compound 8]

Compound 8 was synthesized in accordance with the following scheme.

[Chemical formula 10]

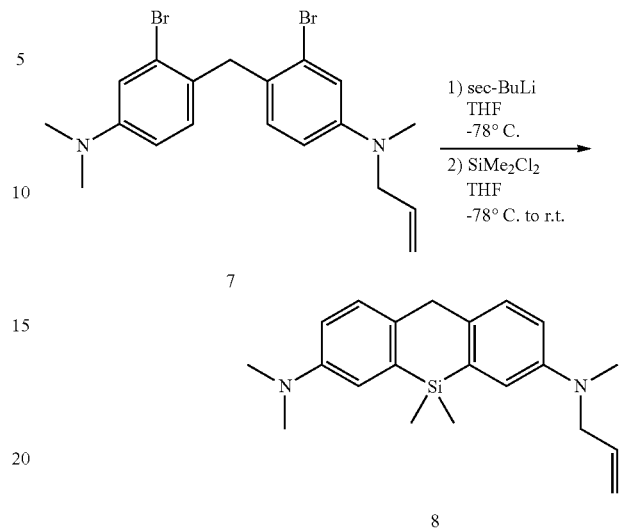

Compound 7 (900 mg, 2.05 mmol, 1 eq.) was dissolved in THF (60 mL) under argon atmosphere and stirred for 15 min. at −78° C. A 1-M sec-butyl lithium cyclohexane/n-hexane solution (6.50 mL, 6.50 mmol, 3.2 eq.) was slowly added over 8 minutes, and the mixture was stirred for 22 minutes. Next, dichlorodimethylsilane (500 μL, 4.18 mmol, 2.0 eq.) THF (13 mL) solution was added and gradually returned to room temperature, and the mixture was stirred for 3 hours. 2 N of hydrochloric acid was added to acidify the mixture, saturated aqueous sodium hydrogen carbonate solution was subsequently added, and THF was removed under reduced pressure. The resulting aqueous layer was extracted using dichloromethane, the organic phase was then washed using water and a saturated sodium chloride solution and dried using anhydrous sodium sulfate, and the solvent was removed under reduced pressure. The resulting residue was purified by medium-pressure silica gel chromatography (eluent: n-hexane/ethyl acetate=100/0 to 94/6) to obtain the objective compound 8 (382 mg, 55%).

$^1$H NMR (400 MHz, CDCl$_3$): δ 0.44 (s, 6H), 2.927-2.93 (m, 9H), 3.90-3.91 (m, 2H), 3.95 (s, 2H), 5.12-5.20 (m, 2H), 5.85 (ddt, 1H, J=17.2, 10.2, 5.2 Hz), 6.69-6.74 (m, 2H), 6.97 (d, 1H, J=2.8 Hz), 6.99 (d, 1H, J=2.8 Hz), 7.15-7.19 (m, 2H); $^{13}$C NMR (100 MHz, CDCl$_3$): δ-2.7, 38.3, 39.2, 41.2, 55.9, 114.0, 114.2, 116.4, 117.4, 117.6, 128.56, 128.58, 134.3, 134.9, 135.3, 136.09, 136.13, 147.5, 148.8; HRMS (ESI$^+$): Calcd for [M+H]$^+$, 337.20945, Found, 337.20957 (+0.1 mmu).

[Synthesis of Compound 9]

Compound 9 was synthesized in accordance with the following scheme.

[Chemical formula 11]

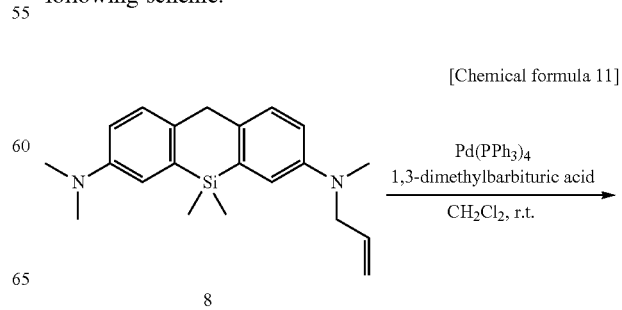

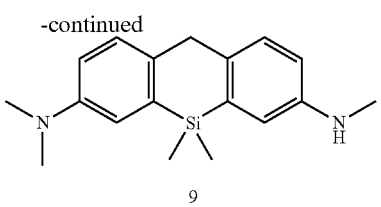

9

Compound 8 (382 mg, 1.13 mmol, 1 eq.) was dissolved in deoxygenated dichloromethane (14 mL), 1,3-dimethyl-barbituric acid (1.48 g, 9.48 mmol, 8.4 eq.) and tetrakis (triphenylphosphine) palladium (274 mg, 237 μmol, 0.2 eq.) were added, and the mixture was stirred at room temperature overnight. A saturated aqueous sodium hydrogen carbonate solution was added and then extracted using dichloromethane, the organic layer was subsequently washed using water and a saturated sodium chloride solution, dried using anhydrous sodium sulfate, and filtered, and the solvent was thereafter removed under reduced pressure. The resulting residue was purified by medium-pressure silica gel chromatography (eluent: n-hexane/ethyl acetate=91/9 to 70/30) to obtain the objective compound 9 (289 mg, 86%).

$^1$H NMR (400 MHz, CDCl$_3$): δ 0.44 (s, 6H), 2.85 (s, 3H), 2.93 (s, 6H), 3.94 (s, 2H), 6.58 (dd, 1H, J=8.1, 2.6 Hz), 6.73 (dd, 1H, J=8.4, 2.8 Hz), 6.85 (d, 1H, J=2.6 Hz), 6.99 (d, 1H, J=2.8 Hz), 7.14 (d, 1H, J=8.1 Hz), 7.18 (d, 1H, J=8.4 Hz); $^{13}$C NMR (100 MHz, CDCl$_3$): δ-2.7, 31.2, 39.4, 41.3, 113.3, 114.3, 117.4, 117.7, 128.6, 128.7, 135.4, 135.7, 136.1, 136.4, 147.1, 148.8; HRMS (ESI$^+$): Calcd for [M+H]$^+$, 297.17815, Found, 297.17853 (+0.4 mmu).

[Synthesis of Compound 11]

Compound 11 was synthesized in accordance with the following scheme. Synthesis of compound 10 is disclosed in J. Le Notre et al., Adv. Synth. Catal. 349, 432 (2007), and synthesis was carried out on the basis thereof.

Compound 9 (102.8 mg, 0.347 mmol, 1 eq.) and compound 10 (756.9 mg, 2.94 mmol, 8.5 eq.) were dissolved in acetonitrile (4 mL), N,N-diisopropylethylamine (512 μL, 2.94 mmol, 8.5 eq.) and a small amount of potassium iodide were added, and the mixture was heated and refluxed for 5.5 hours at 80° C. Water was added and then extracted using dichloromethane, the organic phase was washed using water and a saturated sodium chloride solution and dried using anhydrous sodium sulfate, and the solvent was removed under reduced pressure. The resulting residue was purified by medium-pressure silica gel chromatography (eluent: n-hexane/ethyl acetate=86/14 to 65/35) to obtain the objective compound 11 (91.7 mg, 56%).

$^1$H NMR (400 MHz, CDCl$_3$): δ 0.45 (s, 6H), 1.93 (quin, 2H, J=7.2 Hz), 2.41 (t, 2H, J=7.2 Hz), 2.90 (s, 3H), 2.94 (s, 6H), 3.34 (t, 2H, J=7.2 Hz), 3.95 (s, 2H), 5.10 (s, 2H), 6.68 (dd, 1H, J=8.4, 2.8 Hz), 6.74 (dd, 1H, J=8.4, 2.8 Hz), 6.95 (d, 1H, J=2.8 Hz), 6.99 (d, 1H, J=2.8 Hz), 7.15 (d, 1H, J=8.4 Hz), 7.18 (d, 1H, J=8.4 Hz), 7.31-7.36 (m, 5H); $^{13}$C NMR (100 MHz, CDCl$_3$): δ-2.7, 22.4, 31.8, 38.6, 39.2, 41.2, 52.4, 66.4, 113.8, 114.2, 117.2, 117.3, 117.7, 128.3, 128.4, 128.5, 128.65, 128.67, 134.8, 136.0, 136.1, 136.2, 147.3, 148.8, 173.2; HRMS (ESI$^+$): Calcd for [M+H]$^+$, 473.26188, Found, 473.26185 (-0.0 mmu).

[Synthesis of Compound 12]

Compound 12 was synthesized in accordance with the following scheme.

[Chemical formula 13]

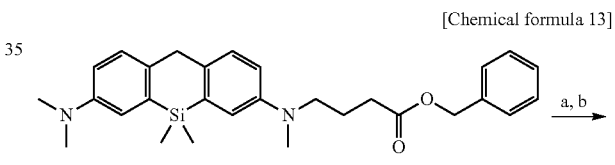

11

[Chemical formula 12]

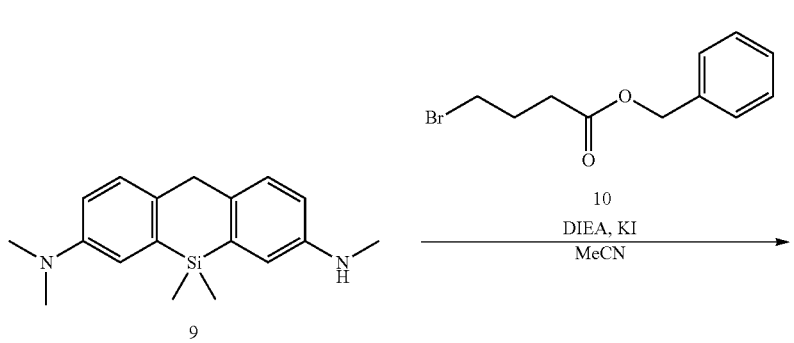

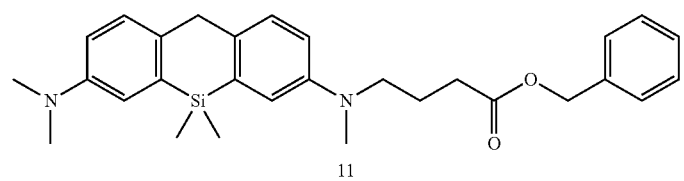

11

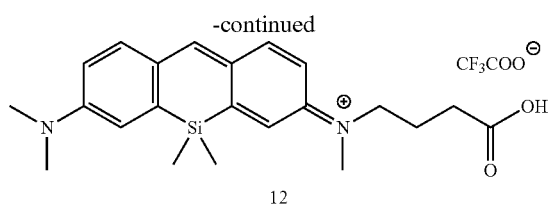

a) Pd/C, H₂, MeOH, r.t., b) DDQ, CH₂Cl₂, r.t.

Compound 11 (171 mg, 0.361 mmol, 1 eq.) was dissolved in methanol, palladium carbon was added, and the mixture was stirred for 2 days at room temperature under a hydrogen atmosphere. The reaction mixture was filtered, and the solvent was removed from the filtrate under reduced pressure. The resulting residue was dissolved in dichloromethane, 2,3-dichloro-5,6-dicyano-p-benzoquinone (180.3 mg, 0.794 mmol, 2.2 eq.) was added, and the mixture was stirred at room temperature overnight. Water was added and then extracted using dichloromethane, the organic phase was washed using water and a saturated sodium chloride solution and dried using anhydrous sodium sulfate, and the solvent was removed under reduced pressure. The resulting residue was purified by HPLC (eluent A (H₂O, 1% acetonitrile, 0.1% trifluoroacetic acid), eluent B (acetcnitrile, 1% H₂O) (A/B=90/10 to 0/100 40 min)) to obtain the objective compound 12 (110 mg, 61%).

$^1$H NMR (400 MHz, CD₃OD): δ 0.54 (s, 6H), 1.95-2.02 (m, 2H), 2.45 (t, 2H, J=6.5 Hz), 3.34 (s, 3H), 3.37 (s, 6H), 3.73-3.77 (m, 2H), 6.98 (dd, 1H, J=9.2, 2.7 Hz), 7.02 (dd, 1H, J=9.1, 2.6 Hz), 7.33 (d, 1H, J=2.2 Hz), 7.51 (m, 1H), 7.71-7.73 (m, 2H, g), 7.87 (s, 1H); $^{13}$C NMR (100 MHz, CD₃CN); δ-1.3, 23.0, 31.1, 35.8, 41.4, 53.1, 115.06, 115.12, 122.3, 122.4, 128.25, 128.31, 144.0, 144.1, 148.42, 148.44, 155.68, 156.17, 160.6, 174.8; HRMS (ESI⁺): Calcd for [M]⁺, 381.19928, Found, 381.19929 (+0.0 mmu).

[Synthesis of Compound 14]

Compound 14 was synthesized in accordance with the following scheme. Synthesis of compound 13 is disclosed in Nat. Biotech., 2003, 21, 86-89, and synthesis was carried out on the basis thereof.

[Chemical formula 14]

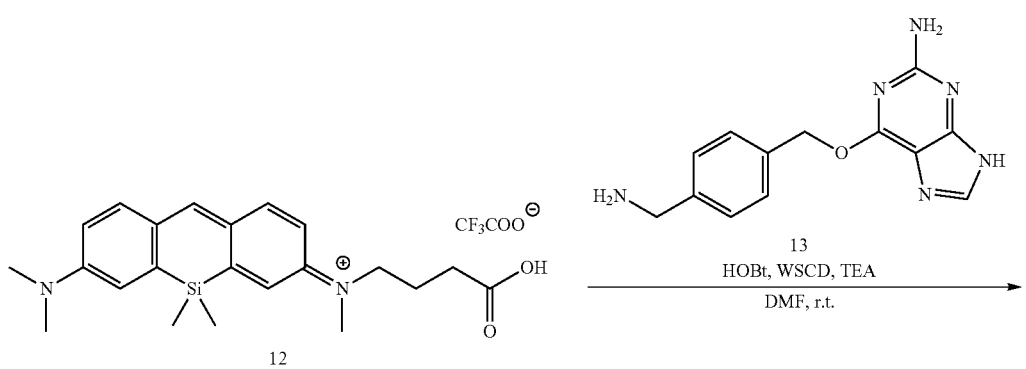

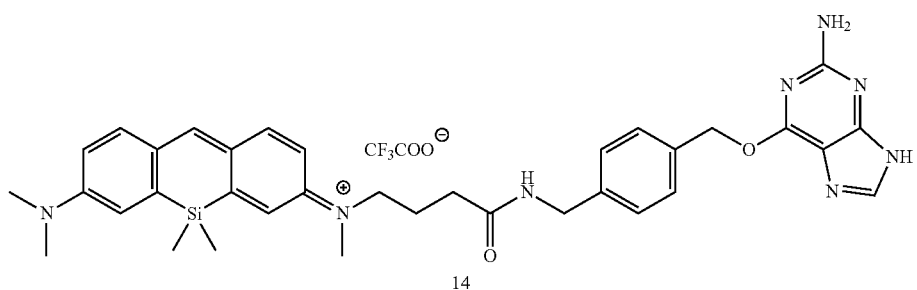

Compound 12 (9.40 mg, 0.0190 mmol, 1 eq.) was dissolved in dewatered N,N-dimethylformamide, compound 13 (7.5 mg, 0.0277 mmol, 1.5 eq.), 1-hydroxybenzotriazole (9.1 mg, 0.0594 mmol, 3.1 eq.), 1-ethyl-3-(3-dimethylaminopropyl) carbodimide hydrochloride (6.6 mg, 0.0344 mmol, 1.8 eq.), and triethylamine (10 μL, 0.0717 mmol, 3.8 eq.) were added, the mixture was stirred for 21 hours at room temperature under an argon atmosphere, and thereafter compound 13 (2.3 mg, 0.00850 mmol, 0.45 eq.) was added, and the mixture was stirred for another 24 hours. The solvent was removed under reduced pressure, the resulting residue was purified by HPLC (eluent A (H₂O, 1% acetonitrile, 0.1% trifluoroacetic acid), eluent B (acetonitrile, 1% H₂O) (A/B=90/10 to 0/100 40 min)) to obtain the objective compound 14 (7.5 mg, 53%).

¹H NMR (400 MHz, CD₃OD): δ 0.52 (s, 6H), 1.99-2.06 (m, 2H), 2.38 (t, 2H, J=6.3 Hz), 3.33 (s, 3H), 3.37 (s, 6H), 3.70-3.74 (m, 2H), 4.41 (s, 2H), 5.63 (s, 2H), 6.56-7.00 (m, 2.4), 7.31 (d, 1H, J=2.3 Hz), 7.35 (d, 2H, J=8.1 Hz), 7.41 (br s 1H), 7.52 (d, 2H, J=8.1 Hz), 7.68-7.72 (m, 2H), 7.86 (s, 1H) 8.33 (s, 1H); ¹³C NMR (100 MHz, CD₃OD): δ-1.4, 24.0, 33.1, 39.5, 41.0, 43.8, 53.4, 70.8, 108.2, 115.3, 122.3, 122.4, 128.36, 128.95, 128.98, 130.2, 135.4, 141.0, 143.5, 144.5, 144.6, 149.0, 149.1, 153.7, 156.2, 156.8, 158.3, 161.09, 161.11, 161.7, 174.6; HRMS (ESI⁺): Calcd for [M]⁺, 633.31163, Found, 633.31169 (+0.1 mmu).

[Synthesis of Compound 16]

Compound 16 was synthesized in accordance with the following scheme. Synthesis of compound 15 noted below is disclosed in J. Am. Chem. Soc. 2013, 135, 6184-6191, and synthesis was carried out on the basis thereof.

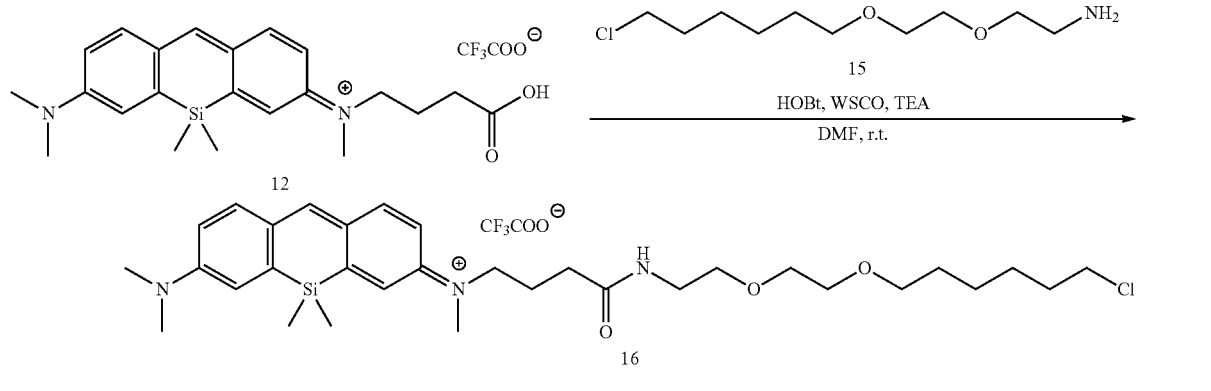

Compound 12 (11.3 mg, 0.0228 mmol, 1 eq.) was dissolved in dewatered N,N-dimethylformamide (1.5 mL), compound 15 (9.1 mg, 0.0407 mmol, 1.8 eq.), 1-hydroxybenzotriazole (6.1 mg, 0.0451 mmol, 2.0 eq.), 1-ethyl-3-(3-dimethylaminopropyl) carbodiimide hydrochloride (7.2 mg. 0.0375 mmol, 1.6 eq.), and triethylamine (14.3 μL, 0.103 mmol, 4.5 eq.) were added at 0° C., the mixture was gradually returned to room temperature under an argon atmosphere and stirred overnight. The solvent was removed under reduced pressure, the resulting residue was purified by HPLC (eluent A (H₂O, 1% acetonitrile, 0.1% trifluoroacetic acid), eluent B (acetonitrile, 1% H₂O) (A/B=90/10 to 0/100 40 min)) to obtain the objective compound 16 (9.21 mg, 58%).

¹H NMR (400 MHz, CD₃OD): δ 0.55 (s, 6H), 1.32-1.44 (m, 4H), 1.55 (quin, 2H, J=7.0 Hz), 1.72 (quin, 2H, J=7.0 Hz), 1.93-2.05 (m, 2H), 2.33 (t, 2H, J=6.8 Hz), 3.34 (s, 3H), 3.38 (s, 6H), 3.44 (t, 2H, J=6.6 Hz), 3.50-3.60 (m, 10H), 3.73 (t, 2H, J=7.7 Hz), 6.98-7.03 (m, 2H), 7.33 (d, 1H, J=2.5 Hz), 7.41 (br s, 1H), 7.71-7.73 (m, 2H), 7.88 (s, 1H); ¹³C NMR (100 MHz, CD₃OD): δ-1.4, 24.0, 26.5, 27.7, 30.5, 33.2, 33.7, 39.6, 40.4, 41.0, 45.7, 53.4, 70.5, 71.21, 71.24, 72.2, 115.26, 115.29, 122.3, 122.4, 128.97, 129.00, 144.57, 144.60, 149.0, 145.1, 156.2, 156.8, 161.1, 174.8; HRMS (ESI⁺): Calcd for [M]⁺, 586.32262, Found, 586.32267 (+0.0 mmu).

Synthesis of Compound 17

Compound 17 was synthesized in accordance with the following scheme.

[Chemical formula 16]

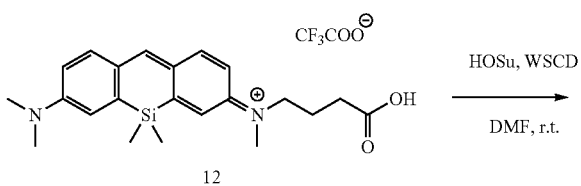

[Chemical formula 15]

-continued

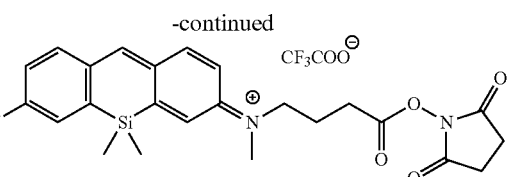

Compound 12 (7.0 mg, 0.0142 mmol, 1 eq.) was dissolved in dewatered N,N-dimethylformamide (5 mL), N-hydroxysuccinimide (8.7 mg, 0.0756 mmol, 5.3 eq.) and 1-ethyl-3-(3-dimothylaminopropyl) carbodiimide hydrochloride (6.1 mg, 0.0318 mmol, 2.2 eq.) were added, the mixture was stirred for 33 hours at room temperature under an argon atmosphere, N-hydroxysuccinimide (9.8 mg, 0.0852 mmol, 6.0 eq.) and 1-ethyl-3-(3-dimethylaminopropyl) carbodiimide hydrochloride (11.1 mg, 0.0579 mmol, 4.1 eq.) were added, and the mixture was stirred for another 43 hours. The solvent was removed under reduced pressure, the resulting residue was purified by HPLC (eluent A (H₂O, 1% acetonitrile, 0.1% trifluoroacetic acid), eluent B (acetonitrile, 1% H₂O) (A/B=90/10 to 0/100 40 min.)) to obtain the objective compound 17 (1.7 mg, 20%).

¹H NMR (400 MHz, CD₃OD): δ 0.53 (s, 6H), 2.10-2.17 (m, 2H), 2.32 (t, 2H, J=6.6 Hz), 2.87 (s, 4H), 3.36 (s, 3H), 3.38 (s, 6H), 3.80-3.84 (m, 2H), 6.98-7.04 (m, 2H), 7.34 (d, 1H, J=2.6 Hz), 7.38 (d, 1H, J=2.4 Hz), 7.71-7.74 (m, 2H), 7.89 (s, 1H); ¹³C NMR (100 MHz, CD₃OD): δ-1.5, 23.2, 26.5, 28.7, 39.5, 41.1, 52.6, 115.3, 115.4, 122.1, 122.4, 129.0, 129.1, 144.6, 144.8, 148.9, 149.4, 156.1, 156.9, 161.4, 170.2, 171.8; HRMS (ESI$^+$): Calcd for [M]$^+$, 478.21566, Found, 478.21559 (−0.1 mmu).

[Synthesis of Compound 19]

Compound 19 was synthesized in accordance with the following scheme.

[Chemical formula 17]

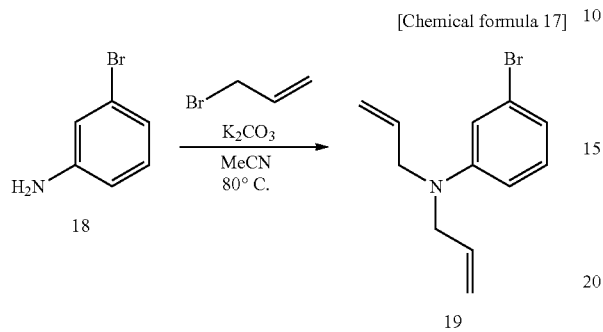

Potassium carbonate (11.96 g, 86.54 mmol, 2.5 eq.) was suspended in acetonitrile (40 mL), 3-bromoaniline (5.96 g, 34.65 mmol, 1 eq.) and allyl bromide (21.89 g, 180.9 mmol, 5.2 eq.) were added, and the mixture was heated and refluxed at 80° C. for 26 hours while being stirred. The reaction mixture was returned to room temperature and then filtered through celite, the filtration residue and celite were washed using ethyl acetate, and the solvent was removed under reduced pressure from a mixture of filtrate and washing solution. The resulting residue was purified by medium-pressure silica gel chromatography (eluent: n-hexane/ethyl acetate=100/0 to 89/11) to obtain the objective compound 19 (5.68 g, 22.5 mmol, 65%).

$^1$H NMR (400 MHz, CDCl$_3$): δ 3.93-3.95 (m, 4H), 5.20-5.25 (w, 4H), 5.83-5.93 (m, 2H), 6.64-6.67 (m, 1H), 6.84-6.89 (m, 2H), 7.06-7.10 (m, 1H); $^{13}$C NMR (100 MHz, CDCl$_3$): δ 52.7, 110.9, 115.0, 116.3, 119.1, 123.4, 130.3, 133.3, 149.9; HRMS (ESI$^+$): Calcd for [M+H]$^+$, 252.03824, Found, 252.03819 (−0.1 mmu).

[Synthesis of Compound 21]

Compound 21 was synthesized in accordance with the following scheme.

[Chemical formula 18]

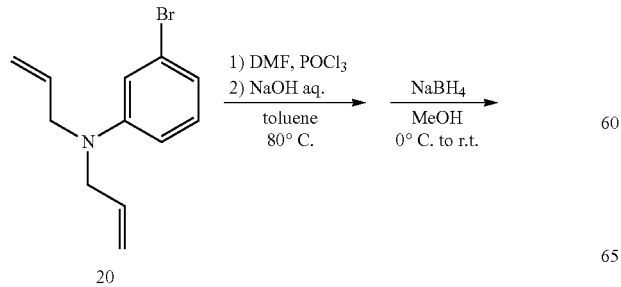

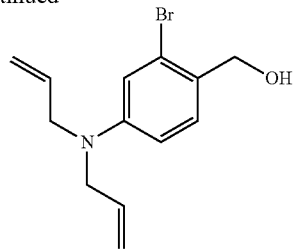

In a flask having argon gas sealed therein, compound 20 (1.57 g, 6.22 mmol, 1 eq.) was dissolved in toluene (10 mL), N,N-dimethylformamide (700 μL, 9.04 mmol, 1.5 eq.) and phosphoryl chloride (700 μL, 7.51 mmol, 1.2 eq.) were added, and the mixture was stirred for 3.5 hours at 80° C. The mixture was returned to room temperature, an aqueous solution of 2N sodium hydroxide was added, and the toluene was removed under reduced pressure from the mixed solution. The resulting aqueous layer was extracted using dichloromethane, the organic layer was subsequently washed using a saturated sodium chloride solution and dried using anhydrous sodium sulfate, and the solvent was removed under reduced pressure. The resulting residue was dissolved in methanol, sodium borohydride (376.5 mg, 9.95 mmol, 1.6 eq.) was added at 0° C., and the mixture was stirred for 10 minutes. Water was added and then extracted using dichloromethane, the organic layer was then washed using a saturated sodium chloride solution and dried using anhydrous sodium sulfate, and the solvent was removed under reduced pressure. The resulting residue was purified by medium-pressure silica gel chromatography (eluent: n-hexane/ethyl acetate=83/17 to 62/38) to obtain the objective compound 21 (740 mg, 2.62 mmol, 42%).

$^1$H NMR (400 MHz, CDCl$_3$): δ 3.89-3.90 (m, 4H), 4.59 (s, 2H), 5.13-5.19 (m, 4H), 5.82 (ddt, 2H, J=17.0, 10.5, 4.8 Hz), 6.60 (dd, 1H, J=8.5, 2.6 Hz), 6.86 (d, 1H, J=2.6 Hz), 7.20 (d, 1H, J=8.5 Hz); $^{13}$C NMR (100 MHz, CDCl$_3$): δ 52.7, 64.8, 111.4, 115.9, 116.4, 124.3, 127.1, 130.3, 133.2, 149.3; HRMS (ESI$^+$): Calcd for [M+Na]$^+$, 304.03075, Found, 304.03081 (+0.1 mmu).

[Synthesis of Compound 23]

Compound 23 was synthesized in accordance with the following scheme.

[Chemical formula 19]

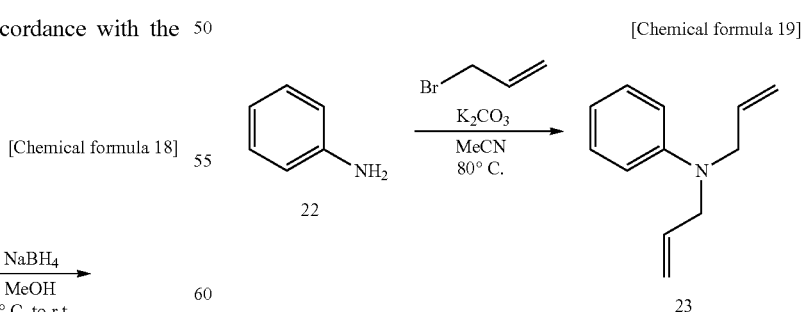

Potassium carbonate (9.53 g, 68.97 mmol, 2.1 eq.) was suspended in acetonitrile (30 mL), aniline (3.07 g, 32.96 mmol, 1 eq.) and allyl bromide (10.28 g, 85.01 mmol, 2.6 eq.) were added, and the mixture was heated and refluxed at 80° C. for 5 hours while being stirred. Allyl bromide (2.58 g, 21.29 mmol, 0.6 eq.) was added, and the mixture was thereafter stirred, heated, and refluxed for another 13 hours at 80° C. The mixture was returned to room temperature, the reaction mixture was then filtered through celite, the filtration residue and celite were washed using ethyl acetate, and the solvent was removed under reduced pressure from the mixture of filtrate and washing solution. The resulting residue was purified by rnediura-pressure silica gel chromatography (eluent: n-hexane/ethyl acetate=100/0 to 97/3) to obtain the objective compound 23 (5.35 g, 30.9 mmol, 94%).

$^1$H NMR (400 MHz, CDCl$_3$): δ 3.86-3.68 (m, 4H), 5.10-5.18 (m, 4H), 5.82 (ddt, 2H, J=17.2, 10.3, 4.5 Hz), 6.64-6.68 (m, 3H), 7.14-7.19 (m, 2H); $^{13}$C NMR (100 MHz, CDCl$_3$): δ 52.0, 112.4, 116.0, 116.4, 129.1, 134.1, 148.7; HRMS (ESI$^+$): Calcd for [M+H]$^+$, 174.12773, Found, 174.12967 (+0.9 mmu).

[Synthesis of Compound 25]

Compound 25 was synthesized in accordance with the following scheme.

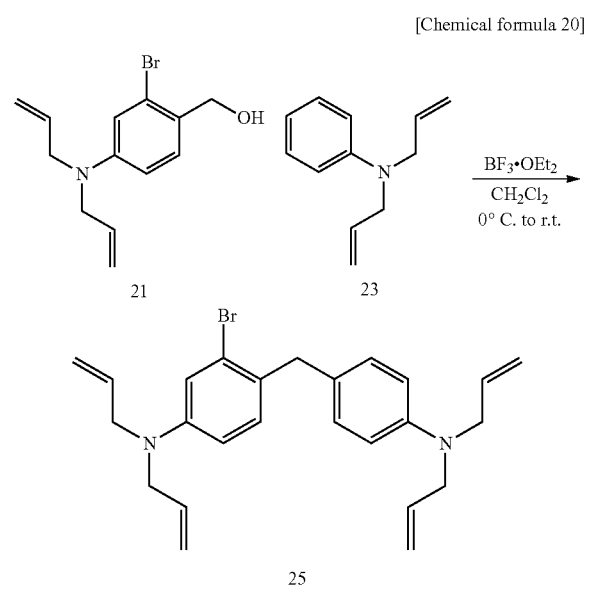

Compound 21 (386.0 mg, 1.368 mmol, 1.1 eq.) and compound 23 (218.8 mg, 1.263 mmol, 1 eq.) were dissolved in dewatered dichloromethane (10 mL), a boron trifluoride diethyl ether complex (500 μL, 4.051 mmol, 3.2 eq.) was gradually added at 0° C. and stirred for 10 minutes, and the mixture was thereafter returned to room temperature and stirred for another 3 hours. A saturated aqueous sodium hydrogen carbonate solution was added and then extracted using dichloromethane, the organic layer was then washed using a saturated sodium chloride solution and dried using anhydrous sodium sulfate, and the solvent was removed under reduced pressure. The resulting residue was purified by medium-pressure silica gel chromatography (eluent: n-hexane/ethyl acetate=100/0 to 88/12) to obtain the objective compound 25 (395.2 mg, 0.903 mmol, 72%).

$^1$H NMR (400 MHz, CDCl$_3$): δ 3.90-3.94 (m, 10H), 5.17-5.25 (m, 83), 5.82-5.94 (m, 4H), 6.60 (dd, 1H, J=8.6, 2.7 Hz), 6.67-6.70 (m, 2H), 6.93 (d, 1H, J=2.7 Hz), 6.98 (d, 1H, J=8.6 Hz), 7.08 (d, 2H, J=8.6 Hz); $^{13}$C NMR (100 MHz, CDCl$_3$): δ 39.7, 52.9, 53.0, 111.9, 112.6, 116.06, 116.12, 116.3, 125.5, 128.4, 128.6, 129.6, 131.1, 133.7, 134.4, 147.2, 148.1; HRMS (ESI$^+$): Calcd for [M+H]$^+$, 437.15969, Found, 437.15873 (+0.0 mmu).

[Synthesis of Compound 26]

Compound 26 was synthesized in accordance with the following scheme.

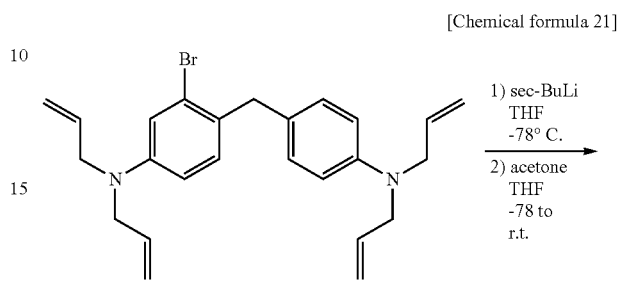

In a flask having argon sealed therein, compound 25 (208.5 mg, 0.477 mmol, 1 eq.) was dissolved in dewatered tetrahydrofuran (15 mL), and cooled to −78° C. while being stirred. A 1-M sec-butyl lithium cyclohexane/n-hexane solution (1.0 mL, 1.0 mmol, 2.1 eq.) was added gradually, and the mixture was stirred for 10 minutes. Dewatered acetone (210 μL, 2.85 mmol, 6.0 eq.) was then added gradually, the mixture was stirred for 15 minutes still at −78° C., and the mixture was thereafter returned to room temperature, and stirred for another 5 hours. A saturated aqueous solution of ammonium chloride was added and tetrahydrofuran was thereafter removed under reduced pressure. The resulting aqueous phase was extracted using dichloromethane, the organic layer was then washed using a saturated sodium chloride solution and dried using anhydrous sodium sulfate, and the solvent was removed under reduced pressure. The resulting residue was purified by medium-pressure silica gel chromatography (eluent: n-hexane/ethyl acetate=89/11 to 68/32) to obtain the objective compound 26 (125.8 mg, 0.302 mmol, 63%).

$^1$H NMR (400 MHz, CDCl$_3$): δ 1.61 (s, 6H), 1.77 (s, 1H), 3.87-3.89 (m, 4H), 3.91-3.92 (m, 4H), 4.17 (s, 2H), 5.12-5.23 (m, 8H), 5.80-5.92 (m, 4H), 6.57 (dd, 1H, J=8.5, 2.7 Hz), 6.62 (d, 2H, J=8.7 Hz), 6.83 (d, 1H, J=2.7 Hz), 6.94-6.98 (m, 3H); $^{13}$C NMR (100 MHz, CDCl$_3$): δ 31.9, 33.0, 53.0, 53.2, 74.3, 110.3, 111.4, 112.7, 116.1, 116.2, 126.5, 129.4, 130.9, 134.0, 134.5, 134.6, 146.6, 146.9, 147.0; HRMS (ESI$^+$): Calcd for [M+H]$^+$, 417.29004, Found, 417.29000 (−0.0 mmu).

[Synthesis of Compound 27]

Compound 27 was synthesized in accordance with the following scheme.

[Chemical formula 22]

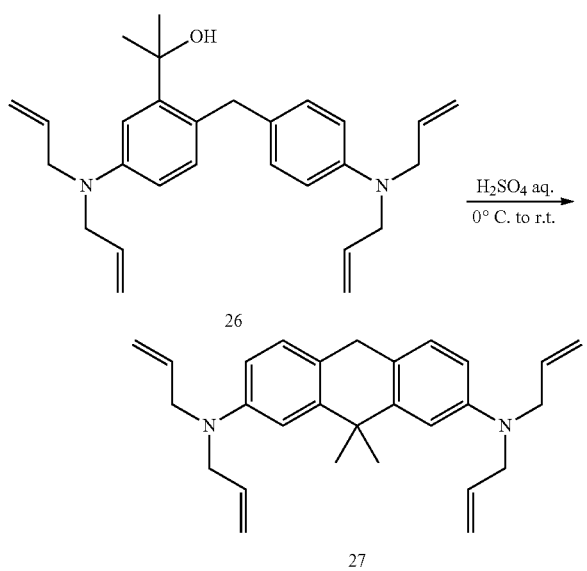

At 0° C., 80% sulfuric acid was added to compound 26 (188.5 mg, 0.452 mmol, 1 eq.), and the mixture was stirred for 30 minutes, then returned to room temperature, and stirred vigorously for another 30 minutes. Water was added and then extracted using dichloromethane, the organic layer was then washed using a saturated sodium hydroxide solution and dried using anhydrous sodium sulfate, and the solvent was removed under reduced pressure to obtain the objective compound (177.2 mg, 0.445 mmol, 98%).

$^1$H NMR (400 MHz, CD$_3$OD): δ1.49 (s, 6H), 3.80 (s, 2H), 3.91-3.93 (m, 8H), 5.12-5.21 (m, 8H), 5.89 (ddt, 4H, J=17.2, 10.3, 5.0 Hz), 6.57 (dd, 2H, J=8.3, 2.6 Hz), 6.90 (d, 2H, J=2.6 Hz), 7.02 (d, 2H, J=0.3 Hz); $^{13}$C NMR (100 MHz, CD$_2$OD): δ29.4, 34.6, 40.6, 54.6, 110.7, 112.2, 116.3, 126.0, 129.1, 136.1, 146.7, 148.8; HRMS (ESI$^+$): Calcd for [M+H]$^+$, 399.27948, Found, 399.27955 (+0.1 mmu).

[Synthesis of Compound 28]

Compound 28 was synthesized in accordance with the following scheme.

[Chemical formula 23]

Argon was sealed in a flask which contains 1,3-dimethyl barbituric acid (60.55 mg, 0.388 mmol, 27 eq.) and tetrakis (triphenylphosphine) palladium (7.8 mg, 0.00675 mmol, 0.47 eq.), compound 27 (5.7 mg, 0.0143 mmol, 1 eq.) dissolved in deoxygenated dichloromethane (7 mL) was added, and the mixture was stirred overnight at room temperature. A saturated aqueous sodium hydrogen carbonate solution was added and extracted using dichloromethane, the organic layer was then washed using a saturated sodium chloride solution, dried using anhydrous sodium sulfate, and filtered, and the solvent was thereafter removed under reduced pressure. The resulting residue was dissolved in dichloromethane, p-chloranil (20.0 mg, 0.0813 mmol, 5.7 eq.) was added, and the mixture was stirred for 1 hour at room temperature. Water was added and then extracted using dichloromethane, the organic layer was then washed using a saturated sodium chloride solution, dried using anhydrous sodium sulfate, and filtered, and the solvent was then removed under reduced pressure. The resulting residue was purified by HPLC (eluent A (H$_2$O, 1% acetonitrile, 0.1% trifluoroacetic acid), eluent B (acetonitrile, 1% H$_2$O) (A/B=50/10 to 0/100 40 min)) to obtain the objective compound 28 (2.1 mg, 0.00595 mmol, 42%).

$^1$H NMR (400 MHz, CD$_3$OD): δ 1.63 (s, 6H), 6.77 (dd, 2H, J=8.7, 2.0 Hz), 7.08 (dd, 2H, J=2.0, 0.8 Hz), 7.63 (d, 2H, J=8.7 Hz), 8.06 (s, 1H); $^{13}$C NMR (100 MHz, CDCl$_3$): δ33.5, 42.6, 114.1, 116.0, 122.1, 141.6, 156.2, 159.5, 161.4; HRMS (ESI$^+$): Calcd for [M]$^+$, 237.13862, Found, 237.13854 (−0.1 mmu).

[Synthesis of Compound 29]

Compound 29 was synthesized in accordance with the following scheme.

[Chemical formula 24]

Argon was sealed in a flask which contains 1,3-dimethyl-barbituric acid (2.99 g, 15.14 mmol, 25 eq.) and tetrakis (triphenylphosphine) palladium (181.0 mg, 0.157 mmol, 0.2 eq.), then compound 27 (307.0 mg, 0.770 mmol, 1 eq.) dissolved in deoxygenated dichloromethane (15 mL) was added The mixture was stirred for 4 hours at room temperature. A saturated aqueous sodium hydrogen carbonate solution was added and extracted using dichloromethane, the organic layer was then washed using a saturated sodium chloride solution, dried using anhydrous sodium sulfate, and filtered, and the solvent was thereafter removed under reduced pressure. The resulting residue was purified by HPLC (eluent A (H$_2$O, 1% acetonitrile, 0.1% trifluoroacetic acid), eluent B (acetonitrile, 1% H₂O) (A/B=90/10 to 0/100 40 min)) to obtain the objective compound 29 (157.0 mg, 0.65 mmol, 86%).

[Synthesis of Compound 31]

Compound 31 was synthesized in accordance with the following scheme.

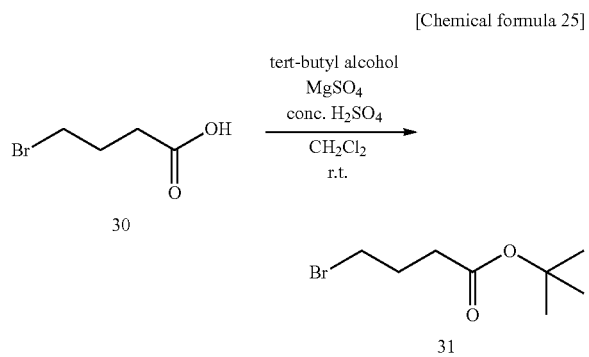

[Chemical formula 25]

4-bromo-butyric acid (2.57 g, 15.39 mmol, 1 eq.) was dissolved in dichloromethane (20 mL), magnesium sulfate (7.74 g, 64.30 mmol, 4.2 eq.), tert-butyl alcohol (5.70 g, 76.95 mmol, 5 eq.), and concentrated sulfuric acid (0.25 mL) were added, and the mixture was stirred for 2 days at room temperature. A saturated aqueous sodium hydrogen carbonate solution was added and extracted using dichloromethane, the organic layer was then washed using a saturated sodium chloride solution and dried using anhydrous sodium sulfate, and the solvent was removed under reduced pressure. The resulting residue was purified by medium-pressure silica gel chromatography (eluent: n-hexane/ethyl acetate=50/50) to obtain the objective compound 31 (1.17 g, 5.24 mmol, 47%).

¹H NMR (400 MHz, CDCl₃): δ 1.27 (s, 9H), 1.91-1.98 (m, 2H), 2.22 (t, 2H, J=7.2 Hz), 3.27 (t, 2H, J=6.5 Hz); ¹³C NMR (100 MHz, CDCl₃): δ 27.9, 28.0, 32.8, 33.7, 80.5, 171.7.

[Synthesis of Compound 32]

Compound 32 was synthesized in accordance with the following scheme.

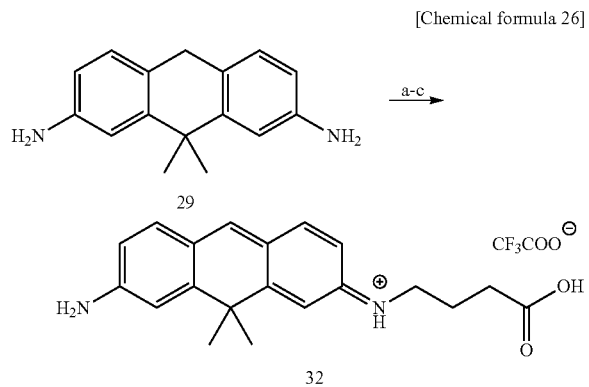

[Chemical formula 26]

Compound 29 (31.0 mg, 0.130 mmol, 1 eq.) was dissolved in acetonitrile (2 mL), compound 31 (22.3 mg, 0.100 mmol, 0.8 eq.), N,N-diisopropylethylamine (113.3 µL, 0.650 mmol, 5 eq.), and a small amount of potassium iodide were added, and the mixture was stirred for 21 hours at 60° C., and then was stirred for another 7 hours at 80° C. The mixture was returned to room temperature, and water was then added and extracted using dichloromethane, then the organic layer was washed using a saturated sodium chloride solution and dried using anhydrous sodium sulfate, and the solvent was removed under reduced pressure. The resulting residue was dissolved in dichloromethane (10 mL), trifluoroacetic acid (2 mL) was added, the mixture was stirred for 2 hours at room temperature, and thereafter the solvent was removed under reduced pressure. The resulting residue was dissolved in dichloromethane (5 mL) and methanol (2 mL), p-chloranil (34.1 mg, 0.139 mmol, 1.1 eq.) was added, the mixture was stirred for 30 min. at room temperature, and the solvent was thereafter removed under reduced pressure. The resulting residue was purified by HPLC (eluent A (H₂O, 1% acetonitrile, 0.1% trifluoroacetic acid), eluent B (acetonitrile, 1% H₂O) (A/B=90/10 to 0/100 40 min)) to obtain the objective compound 29 (11.7 mg, 0.0268 mmol, 21%).

¹H NMR (400 MHz, CD₃OD): δ 1.65 (s, 6H), 1.94-2.01 (m, 2H), 2.46 (t, 2H, J=7.0 Hz), 3.50 (t, 2H, J=7.2 Hz), 6.77 (dd, 1H, J=2.0, 8.7 Hz), 6.84 (d, 1H, J=8.2 Hz), 7.09 (d, 1H, J=2.0 Hz), 7.15 (br s, 1H), 7.61-7.66 (m, 2H), 8.05 (s, 1H); ¹³C NMR (100 MHz, CD₃OD): δ 25.2, 31.7, 33.6, 43.5, 114.1, 116.0, 122.2, 122.4, 141.4, 155.9, 159.6, 161.2, 176.6; HRMS (ESI⁺): Calcd for [M]⁺, 323.17540, Found, 323.17538 (−0.0 mmu).

[Synthesis of Compound 33]

Compound 33 was synthesized in accordance with the following scheme.

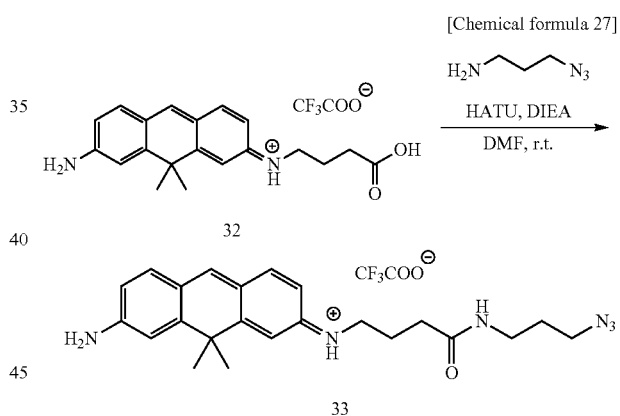

[Chemical formula 27]

Compound 32 (1.1 mg, 0.00252 mmol, 1 eq.) was dissolved in N,N-dimethylformamide (2 mL), then 3-azidopropyl amine (0.74 µL, 0.00756 mmol, 3 eq.), N,N-diisopropylamine (8.8 µL, 0.0504 mmol, 20 eq.), and O-(7-azabenzotriazol-1-yl)-N,N,N',N'-tetramethyluronium hexafluorophosphate salt (5.5 mg, 0.0155 mmol, 6.1 eq.) were added at 0° C., the mixture was stirred for 15 min, then returned to room temperature, and stirred for another 13 hours. The solvent was removed under reduced pressure, the resulting residue was purified by HPLC (eluent A (H₂O, 1% acetonitrile, 0.1% trifluoroacetic acid), eluent B (acetonitrile, 1% H₂O) (A/B=90/10 to 0/100 40 min)) to obtain the objective compound 33 (1.0 mg, 0.00193 mmol, 77%).

¹H NMR (400 MHz, CD₃OD): δ 1.66 (s, 6H), 1.76 (qui, 2H, J=6.7 Hz), 1.99 (qui, 2H, J=7.2 Hz), 2.35 (t, 2H, J=7.2 Hz), 3.27 (t, 2H, J=6.7 Hz), 3.35 (t, 2H, J=6.7 Hz), 3.48 (t, 2H), J=7.2 Hz), 6.77 (dd, 1H, J=2.1, 3.7 Hz), 6.33 (d, 1H, J=3.0 Hz), 7.09-7.11 (m, 2H), 7.11 (brs, 1H), 7.62-7.67 (m, 2H), 8.06 (s, 1H); ¹³C NMR (100 MHz, CD₃OD): δ25.9, 29.7, 33.6, 33.8, 37.8, 40.4, 43.7, 43.7, 50.1, 114.1, 116.0, 122.2, 122.4, 141.5, 155.5, 159.5, 161.3, 175.1; HRMS (ESI$^+$): Calcd for [M]$^+$, 405.24028, Found, 405.23991 (−0.4 mmu).

[Synthesis of Compound 34]

Compound 34 was synthesized in accordance with the following scheme.

acid), eluent B (acetonitrile, 1% H$_2$O) (A/B=90/10 to 0/100 40 min)) to obtain the objective compound 34 (1.3 mg, 0.00189 mmol, 72%).

$^1$H NMR (400 MHz, CD$_3$OD): δ 1.62 (s, 6H), 1.96-2.05 (m, 2H), 2.40 (t, 2H, J=7.0 Hz), 3.44-3.48 (m, 2H), 4.40 (s, 2H), 5.59 (s, 2H), 6.75-6.81 (m, 2H), 7.06-7.03 (m, 2H), 7.33 (d, 2H, J=8.4 Hz), 7.49 (d, 2H, J=8.4 Hz), 7.60-7.65 (m,

[Chemical formula 28]

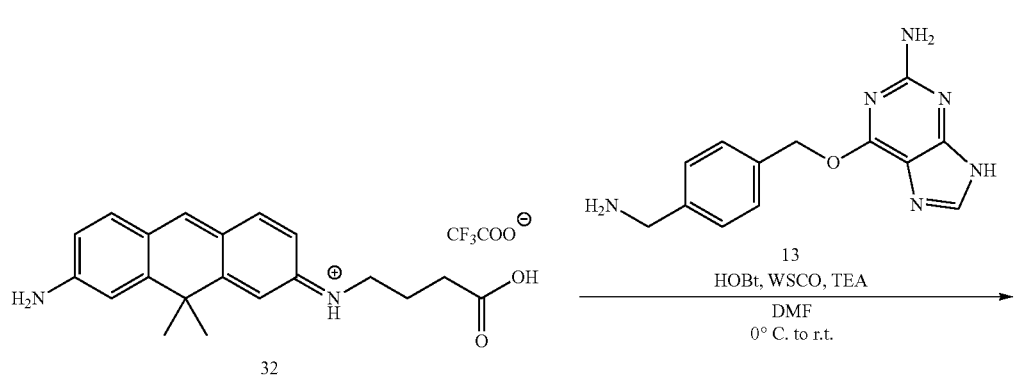

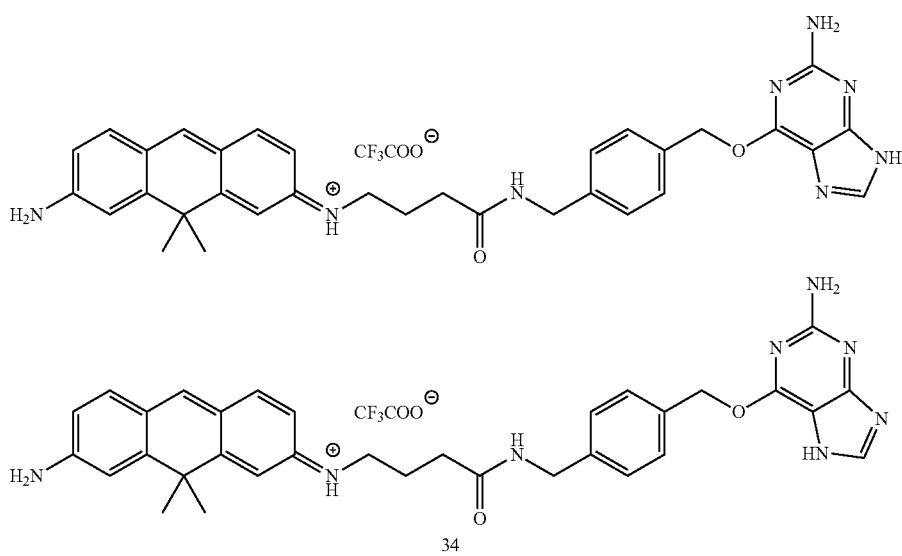

Compound 32 (1.15 mg, 0.00356 mmol, 1 eq.) and compound 13 (3.6 mg, 0.0133 mmol, 3.3 eq.) were dissolved in N,N-dimothylformamido (1.5 mL), then 1-ethyl-3-(3-dimathylaminopropyl) carbodiimide hydrochloride (4.5 mg, 0.0235 mmol, 6.6 eq.), 1-hydroxybenzotriazole (2.0 mg, 0.0148 mmol, 4.2 eq.), and triethylamine (4.96 μL, 0.0356, 10 eq.) were added at 0° C., and the mixture was stirred for 10 minutes, then was returned to room temperature and stirred for another 22 hours. The solvent was removed under reduced pressure, the resulting residue was purified by HPLC (eluent A (H$_2$O, 1% acetonitrile, 0.1% trifluoroacetic 2H), 8.03 (s, 1H), 3.16 (s, 1H); HRMS (ESI$^+$): Calcd for [M]$^+$, 575.28775, Found, 575.28769 (−0.1 mmu).

$^1$H NMR (400 MHz, CD$_3$OD): δ1.62 (s, 6H, f), 1.98-2.05 (m, 2H, 1), 2.40 (t, 2H, J=7.0 Hz, m), 3.44-3.48 (m, 2H, k), 4.39 (s, 2H, o), 5.59 (s, 2H, r), 6.74-6.79 (m, 2H, c, h), 7.06-7.08 (m, 2H, b, i), 7.32 (d, 2H, J=8.0 Hz, q), 7.48 (d, 2H, J=8.0 Hz, p), 7.59-7.64 (m, 2H, d, q), 8.00 (s, 1H, t), 8.02 (s, 1H, e); HRMS (ESI$^+$): Calcd for [M]$^+$, 575.28775, Found, 575.28769 (−0.1 mmu).

[Synthesis of Compound 35]

Compound 35 was synthesized in accordance with the following scheme.

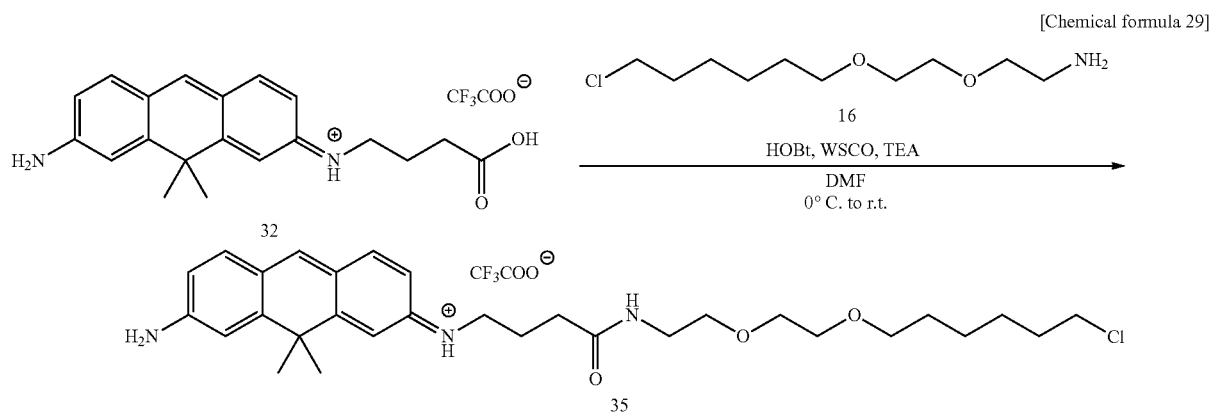

[Chemical formula 29]

Compound 32 (2.3 mg, 0.00711 mmol, 1 eq.) and compound 15 (5.3 mg, 0.0237 mmol, 3.3 eq.) were dissolved in N,N-dimethyl formamide (2 mL), then 1-ethyl-3-(3-dimethylaminopropyl) carbodiimide hydrochloride (3.2 mg, 0.0167 mmol, 2.3 eq.), 1-hydroxybenzotriazole (3.0 mg, 0.0222 mmol, 3.1 eq.), and triethylamino (9.9 μL, 0.0711, 10 eq.) were added at 0° C., the mixture was stirred for 15 minutes, then was returned to room temperature and stirred for another 2 days. The solvent was removed under reduced pressure, the resulting residue was purified by HPLC (eluent A ($H_2O$, 1% acetonitrile, 0.1% trifluoroacetic acid), eluent B (acetonitrile, 1% $H_2O$) (A/B=90/10 to 0/100 40 min)) to obtain the objective compound 35 (1.2 mg, 0.00187 mmol, 36% yield).

$^1$H NMR (400 MHz, $CD_3OD$): δ 1.29-1.43 (m, 4H), 1.563 (qui, 2H, J=7.2 Hz), 1.66 (s, 6H), 1.69-1.77 (m, 2H), 2.00 (qui, 2H, J=7.2 Hz), 2.36 (t, 2H, J=7.2 Hz), 3.37-3.61 (m, 14H), 6.77 (dd, 1H, J=2.0, 8.8 Hz), 6.84 (d, 1H, J=7.6 Hz), 7.09-7.11 (m, 2H), 7.62-7.64 (m, 2H), 8.06 (s, 1H); HRMS (ESI$^+$); Calcd for [M]$^+$, 528.25875, Found, 528.29676 (+0.0 mmu).

Example 2

Calculation of the Dissociation Constant

Absorption spectrum change and fluorescence spectrum change of the probe compounds according to the present invention were measured by adding glutathione. The dissociation constant in a nucleophilic addition-dissociation equilibrium reaction between the probe compounds of the present invention and glutathione was calculated.

FIGS. 1 to 5 show the absorption spectrum change (left) the fluorescence spectrum change (center, excitation wavelengths: 570 nm for compound 2; 620 nm for compounds 5, 14 and 16; and 600 nm for compound 12), and the plot (right) of the glutathione concentration dependence of the absorbance, of compounds 2, 5, 12, 14, and 16, respectively. Measurement was carried out with probe compounds in 1 μM of 1% DMSO aqueous solution. The obtained values of the dissociation contents are shown in Table 1-1 below.

TABLE 1-1

| Probe compound | Dissociation constant |
|---|---|
| Compound 2 | 3.7 μM |
| Compound 5 | 1.5 μM |
| Compound 12 | 3.4 μM |

TABLE 1-1-continued

| Probe compound | Dissociation constant |
|---|---|
| Compound 14 | 6.0 μM |
| Compound 16 | 23 μM |

Figure 6:
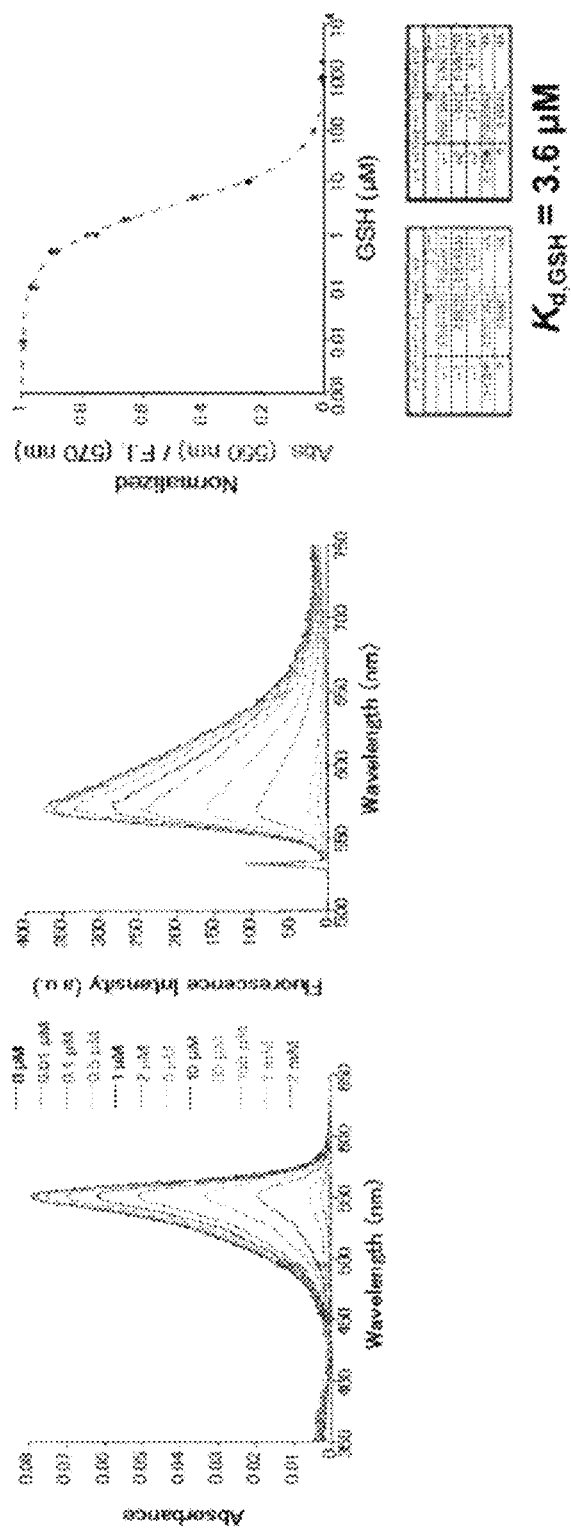
FIG. 6 illustrates the absorption spectrum change (left), the fluorescence spectrum change (center), and a plot of the glutathione concentration dependency of the absorbance and fluorescence intensity (right) in each glutathione concentration of a compound 28, where the compound 28 is the super-resolution fluorescent imaging probe of the present invention.
Figure 7:
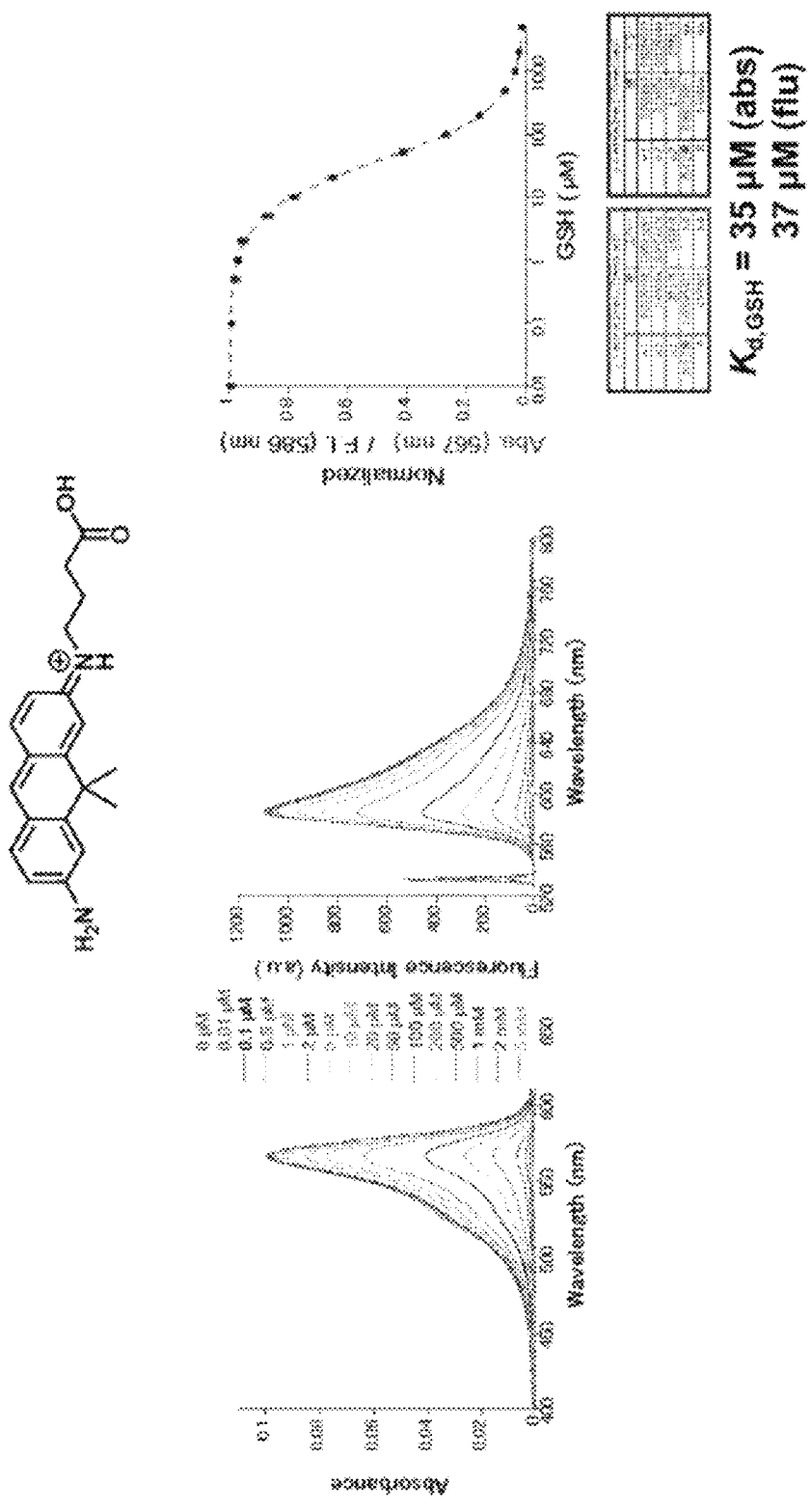
FIG. 7 illustrates the absorption spectrum change (left), the fluorescence spectrum change (center), and a plot of the glutathione concentration dependency of the absorbance and fluorescence intensity (right) in each glutathione concentration of a compound 32, where the compound 32 is the super-resolution fluorescent imaging probe of the present invention.

Similarly, FIGS. 6 and 7 show the absorption spectrum change (left), fluorescence spectrum change (center; excitation wavelength: 530 nm), and the plot (right) of the glutathione concentration dependence of absorbance and fluorescence intensity, of compounds 28 and 32, respectively. Measurement was carried out with probe compounds in 1 μM of 1% DMSO aqueous solution. The obtained values of the dissociation constants are shown in Table 1-2 below.

TABLE 1-2

| Probe compound | Dissociation constant |
|---|---|
| Compound 28 | 3.6 μM |
| Compound 32 | 35 μM (absorbance) |
|  | 37 μM (fluorescence intensity) |

The dissociation constants of these compounds are all in a range of 1 to 100 μM, and it was found that the majority are present as a non-fluorescent nucleophile adduct at a glutathione concentration of several millimolars, which is about the same level as in the cell. This result indicates that the abundance ratio of an unreacted probe compound which emits fluorescence and a compound quenched by reaction with glutathione is within a range suitable for super-resolution fluorescent imaging by SMLM.

Example 3

Calculation of the Reaction Rate

Change over time of transient absorption of the probe compounds of the present invention at various glutathione concentrations was measured using laser flash photolysis, and a nucleophilic addition reaction rate constant k and a nucleophilic addition reaction rime constant T in the nucleophilic addition-dissociation equilibrium reaction between glutathione and the probe compounds of the present invention were calculated. The solution conditions were 14 DMSO aqueous solution and pH 7.4 (10 mM sodium phosphate buffer). A measurement condition was 295 K and a light source was a 10 mJ/pulse XeCl excimer laser (303 nm). The results obtained for compounds 2, 5, 12, 28, and 32 are shown in Tables 2 to 6, respectively.

TABLE 2

Compound 2

| Glutathione concentration (mM) | $k\ (s^{-1})$ | $\tau$ (ms) |
|---|---|---|
| 0.5 | 1.21 | 823 |
| 1 | 2.05 | 487 |
| 5 | 11.0 | 90.7 |
| 10 | 25.0 | 40.1 |

TABLE 3

Compound 5

| Glutathione concentration (mM) | $k\ (s^{-1})$ | $\tau$ (ms) |
|---|---|---|
| 0.1 | 14.3 | 69.9 |
| 0.5 | 95.8 | 10.4 |
| 1 | 176.2 | 5.67 |
| 5 | 976 | 1.02 |
| 10 | 2290 | 0.436 |

TABLE 4

Compound 12

| Glutathione concentration (mM) | $k\ (s^{-1})$ | $\tau$ (ms) |
|---|---|---|
| 0.1 | 7.49 | 134 |
| 0.5 | 42.8 | 23.4 |
| 1 | 75.6 | 13.2 |
| 5 | 444 | 2.25 |
| 10 | 1080 | 0.93 |

TABLE 5

Compound 28

| Glutathione concentration (mM) | $k\ (s^{-1})$ | $\tau$ (ms) |
|---|---|---|
| 0.1 | 21.1 | 47.5 |
| 0.5 | 195 | 5.12 |
| 1 | 371 | 2.69 |
| 5 | 2170 | 0.46 |
| 10 | 5260 | 0.19 |

TABLE 6

Compound 32

| Glutathione concentration (mM) | $k\ (s^{-1})$ | $\tau$ (ms) |
|---|---|---|
| 0.1 | 15.8 | 63.1 |
| 0.5 | 61.7 | 16.2 |
| 1 | 106 | 9.45 |
| 5 | 592 | 1.69 |
| 10 | 1410 | 0.71 |

From the results in Tables 2 to 6, it was found that with the probe compounds of the present invention, the nucleophilic addition of glutathione to the compounds proceeds with a time constant of millisecond order, and that the compounds exhibit fluorescent blinking suitable for super-resolution fluorescent imaging under laser irradiation at 1/10 of conventional intensity or less.

Example 4

Measurement of the Fluorescence Quantum Yield

Fluorescence quantum yield of the probe compounds according to the present invention was measured. The solution conditions were 1 μM probe compound, 1% DMSO aqueous solution, and pH 7.4 (200 mM sodium phosphate buffer). The results obtained for compounds 5, 12, 14, 16, 17, 28, and 32 are indicated in Table 7. It was found that the probe compounds of the invention exhibit a high fluorescence quantum yield suitable for super-resolution fluorescence imaging by SMLM.

TABLE 7

| Probe compound | Fluorescence quantum yield |
|---|---|
| Compound 5 | 0.39 |
| Compound 12 | 0.46 |
| Compound 14 | 0.27 |
| Compound 16 | 0.49 |
| Compound 17 | 0.46 |
| Compound 28 | 0.70 |
| Compound 32 | 0.69 |

Example 5

Multicolor Super-Resolution Imaging

Super-resolution imaging of cells was carried out using antibodies labeled with the probe compounds of the present invention.

1. Labeling Antibodies with Probes

Compound 17, which is a probe compound having a succinimidyl ester introduced to a terminus of compound 5, was dissolved in DMSO, and 1 mM and 10 mM stock solutions were prepared. A goat-derived anti-mouse secondary antibody (IgG, Sigma-Aldrich Co.) for indirect immunostaining of β-tubulin, and a goat-derived anti-rabbit secondary antibody (IgG, Jackson ImmunoResearch Inc.) for indirect immunostaining of Tom20 wore each mixed at room temperature for 30 minutes with compound 17 in 0.2 M of a sodium phosphate buffer (pH 8.5). The antibodies labeled with the probe compound were purified by PD MiniTrap™ G-25 (GE Healthcare) using a phosphate-buffered physiological saline solution (PBS) as the eluent (pH 7.4, GIBCO Inc.). A ratio of the probe compound [mol]/antibody molecule [mol] was calculated as a degree of labeling (DOL) of the probe compound to the antibody. Here, the concentration of the probe compound was calculated from the measured value of absorbance ascribed to the probe compound, and the concentration of the antibody molecules was calculated from the total amount of antibody molecules used in the preparation, assuming no loss of antibody molecules in the purification process. A labeled anti-mouse antibody having a degree of labeling of 2.1, and a labeled anti-rabbit antibody having a degree of labeling of 1.3 were used in super-resolution imaging by SMLM.

Compound 33, which is a probe compound having an azide group introduced at a terminus of compound 28, was also similarly labeled to an antibody. Compound 33 and dibenzo cyclooctene-N-hydroxysuccinimidyl ester (DBCO-NHS, Sigma-Aldrich Co.) were each dissolved in DMSO, and a 10 mM stock solution was prepared. A goat-derived anti-mouse secondary antibody (IgG, Sigma-Aldrich Co.)

for indirect immunostaining of β-tubulin was mixed at room temperature for 30 minutes with the DBCO-NHS in 0.2 M of sodium phosphate buffer (pH 8.5). An antibody (DBCO-IgG) labeled with DBCO-NHS was purified by PD Mini-Trap™ G-25 (GE Healthcare) using a PBS (pH 7.4, GIBCO Inc.) as the eluent. The stock solution of compound 33 was subsequently added to the eluent containing the resulting DBCO-IgG and mixed (room temperature, 30 minutes) in PBS (pH 7.4, GIBCO Inc.). The antibody (DBCO-IgG) labeled with the probe compound was purified by PD MiniTrap™ G-25 (GE Healthcare) using PBS (pH 7.4, GIBCO Inc.) as the eluent.

The ratio of the probe compound [mol]/antibody molecule [mol] was calculated as the degree of labeling (DOL) of the probe compound to the antibody. The concentration of the probe compound was calculated from the measured value of absorbance ascribed to the probe compound, and the concentration of the antibody molecules was calculated from the total amount of antibody molecules used in the preparation, assuming no loss of antibody molecules in the purification process. A labeled antibody having a degree of labeling of 1.4 was used in super-resolution imaging by SMLM.

2. Cell Fixation and Immunostaining

Vero cells derived from the kidney of the African green monkey were cultured (37° C., 5% $CO_2$) in a medium having fetal bovine serum (Invitrogen) an a 1% penicillin-streptomycin solution (Wako Pure Chemical Industries, Ltd.) added to a Dulbecco's modified Eagle's medium (high glucose) that is free of phenol red and contains L-glutamine (GIBCO, Inc.). On the day prior to imaging, the cells were seeded in a Lab-Tek II 8-well chamber cover glass (Thermo Fischer Scientific Inc.). The fixation and immunostaining were performed as fellows with reference to the literature cited below.

M. Bates, G. T. Dempsey, K. H. Chen, X. Zhuang, Multi-color Super-Resolution Fluorescence Imaging via Multi-Parameter Fluorophore Detection. Chetnphyschem: a European journal of chemical physics and physical chemistry 13, 99-107 (2012)

B. Huang, S. A. Jones, B. Brandenburg, X. Zhuang, Whole-cell 3D STORM reveals interactions between cellular structures with nancmeter-scale resolution. Nature methods 5, 1047-1052 (2008)

C. Dellagiacoma et al., Targeted photoswitchable probe for nanoscopy of biological structures. Cherabiochem 11, 1361-1363 (2010)

D. R. Whelan, T. D. Bell, Image artifacts in single molecule localization microscopy: why optimization of sample preparation protocols matters. Scientific reports 5, 7924 (2015)

Fixation with methanol and immunostaining of β-tubulin were carried out as follows. Cells were washed using PBS that was warmed to 37° C. in advance, and were fixed for 5 to 10 minutes using −20° C. methanol containing 5 mM of glycol ether diamine tetraacetic acid (EGTA). The cells were washed 2 to 3 times using BRB80 (80 mM of potassium PIPES buffer containing 1 mM of magnesium chloride and 1 mM of EGTA, pH 6.8) and blocked for 20 minutes using a blocking buffer (PBS containing 1% bovine serum albumin), after which a mouse anti-β-tubulin antibody (TUB2.1, Sigma-Aldrich Corp., T4026, 1/100 dilution) diluted by the blocking buffer was added, and the sample was shaken for 1 hour. The sample was washed twice for 5 minutes each in BRB80 and blocked for 20 minutes using the blocking buffer. Next, immunostaining was carried out for 30 minutes using the labeled secondary antibody (10 to 20 μg/mL) that was diluted by the blocking buffer, and the sample was washed twice for 5 minutes each in BRB80 or PBS. Prior to SMLM imaging, the buffer was substituted with 0.2 M of a sodium phosphate buffer containing 1 to 10 mM of GSH (Wako Pure Chemical Industries, Ltd.).

Fixation with paraformaldehyde and glutaraldehyde, and immunostaining of β-tubulin and Tom20 were carried cut as follows. Cells were washed using PBS warmed to 37° C. in advance, and were fixed at room temperature for 10 minutes using PBS containing 3% paraformaldehyde and 0.1% glutaraldehyde. An unreacted aldehyde group and a fluorescent product produced during the fixation operation were reduced using a solution of 0.1% sodium borohydride in PBS, which had been prepared immediately prior to the usage. The sample was washed using PBS, and thereafter underwent blocking and membrane permeabilization for 20 minutes in a blocking buffer (a solution of 3% USA and 0.5% Triton X-100 in PBS). Next, mouse anti-β-tubulin antibody (TUB2.1, Sigma-Aldrich Corp., T4026, 1/100 dilution) diluted by the blocking buffer and/or rabbit anti-Tom20 antibody (Santa Cruz, sc11415, 1/50 dilution) was added, and the sample was shaken for 30 minutes. The sample was thereafter washed using a wash buffer (a solution of 0.2% BSA and 0.1% Triton X-100 in PBS) three times for 10 minutes each. The labeled secondary antibody (10 to 20 μg/mL for β-tubulin; 10 μg/mL for Tom20) was diluted by a blocking buffer, and the sample was stained with the dilution for 30 minutes. The sample was washed three times for 10 minutes each time with a wash buffer, was further washed for 10 minutes using PBS, and was post-fixed for 10 minutes at room temperature using PBS containing 3% paraformaldehyde and 0.1% glutaraldehyde. The sample was thereafter washed three times using PBS. Prior to SMLM imaging, the buffer was substituted with 0.2 M of a sodium phosphate buffer containing 1 to 10 mM of GSH (Wako Pure Chemical Industries, Ltd.).

3. SMLM Imaging

SMLM imaging was carried out at room temperature using an N-STORM apparatus (Nikon Corp.). Excitation of the fluorophores corresponding to compound 17 and compound 33, which are probe compounds, was carried out by total internal reflection illumination or highly inclined thin illumination at 647 nm (40 to 500 $W/cm^2$) and 561 nm (40 to 500 $W/cm^2$), respectively. Image data were recorded at 15 ms/frame or 30 ms/frame, and analyzed by image integration software (NIS-Elements Advanced Research, Nikon Corp.) to thereby construct a super-resolution image. The super-resolution image was reconstructed with only bright points where 150 photons or more, or 200 photons or more, had been detected.

Figure 8:
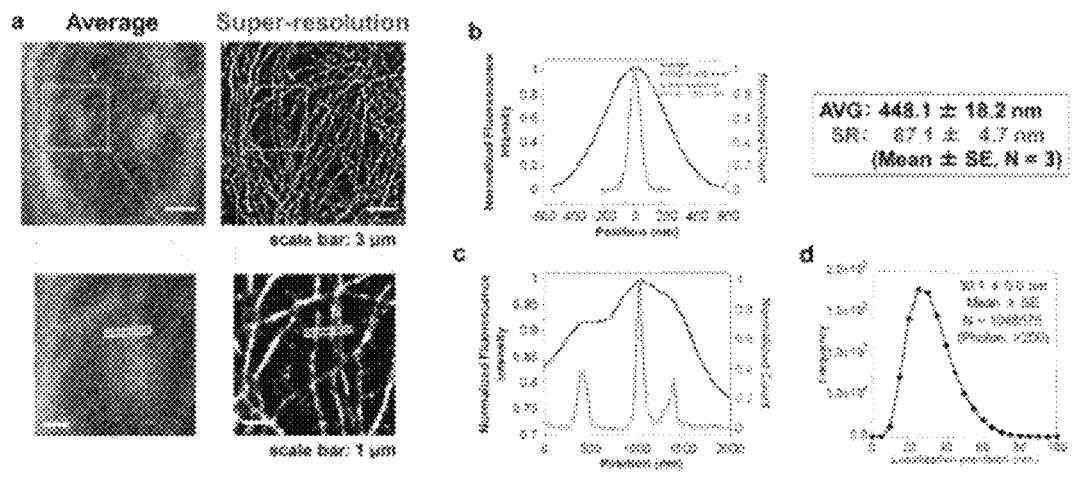
FIG. 8 illustrates results of SMLM imaging of microtubules in fixed Vero cells using an antibody labeled with a compound 17, where the compound 17 is the super-resolution fluorescent imaging probe of the present invention. The figures on the right in FIG. 8a are super-resolution images by SMLM, and the figures on the left illustrate averaged images of fluorescence intensity as a comparison.

FIG. 8 illustrates results of SMLM imaging of microtubules in fixed Vero cells using the antibody labeled with compound 17. The figures on the right in FIG. 8a are super-resolution images by SMLM, and the figures on the left illustrate averaged images of fluorescence intensity as a comparison. FIG. 8b illustrates the cross-sectional profile of normalized fluorescence intensity in the band-like region in the upper figure (scale bar: 3 μm) of the averaged images of FIG. 8a, and the cross-sectional profile of normalized recognized bright points in the band-like region in the upper figure (scale bar: 3 μm) of the super-resolution images of FIG. 8a. FIG. 8c illustrates the cross-sectional profile of normalized fluorescence intensity in the framed region in the lower figure (scale bar: 1 μm) of the averaged images of FIG. 8a, and the cross-sectional profile of normalized recognized bright points in the framed region in the lower figure (scale bar: 1 μm) of the super-resolution images of FIG. 8a. FIG. 8d illustrates the frequency distribution of localization precision in relation to the bright points comprising the upper figure of the super-resolution images of FIG. 8a.

The results shown in FIG. 8 demonstrate the super-resolution imaging of microtubulcs in fixed Vero cells using an antibody labeled with compound 17. The super-resolution images exhibited a higher spatial resolution than the averaged images in terras of line width of the microtubules and separation of adjacent microtubules from each other.

Figure 9:
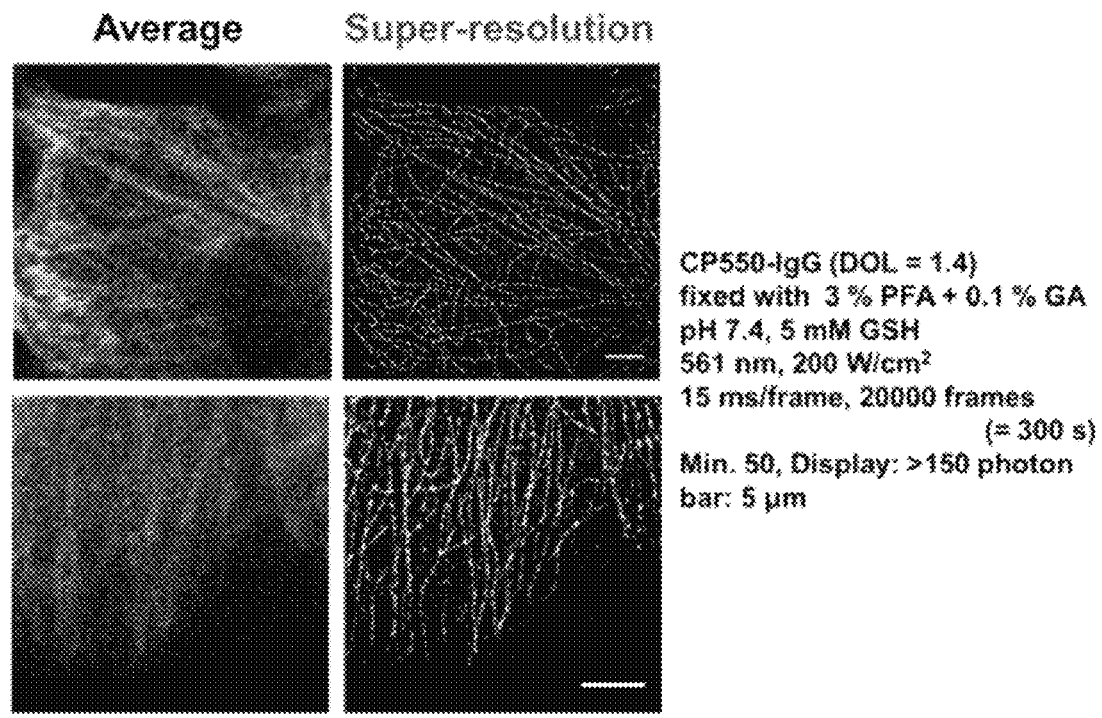
FIG. 9 illustrates results of SMLM imaging of microtubules in fixed Vero cells using an antibody labeled with a compound 33, where the compound 33 is a super-resolution fluorescent imaging probe of the present invention. The figures on the right in FIG. 9 are super-resolution images by SMLM, and the figures on the left illustrate averaged images of fluorescence intensity as a comparison.

FIG. 9 illustrates results of SMLM imaging of microtubules in fixed Vero cells using the antibody labeled with compound 33. The figures on the right in FIG. 9 are super-resolution images by SMLM, and the figures on the left illustrate averaged images of fluorescence intensity as a comparison.

The results shown in FIG. 9 demonstrate the super-resolution imaging of microtubules in fixed Vero cells using the antibody labeled with compound 33. The super-resolution images exhibited a higher spatial resolution than the averaged images in terms of the line width of the microtubules and the separation of adjacent microtubules from each other.

Figure 10:
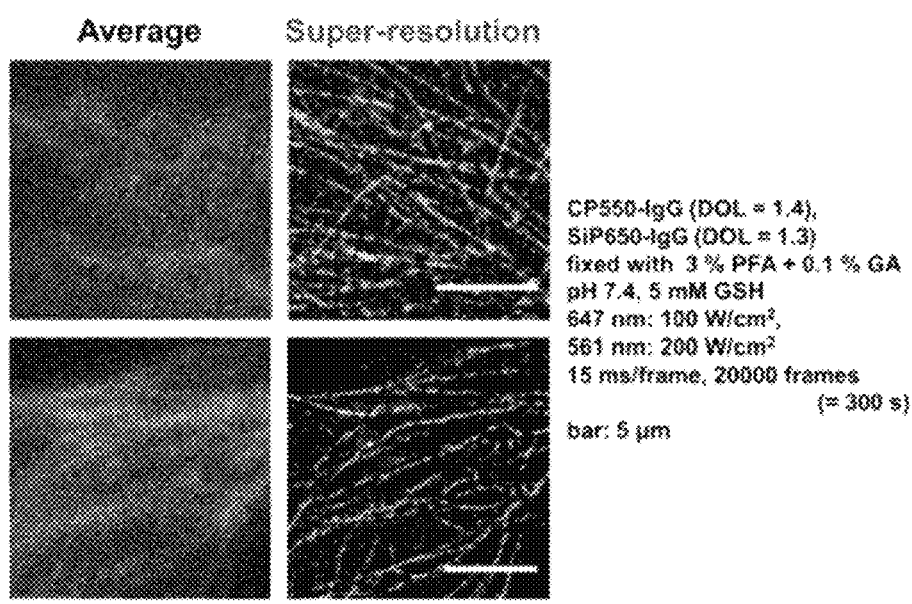
FIG. 10 illustrates results of SMLM imaging in two colors for mitochondria and microtubules in fixed Vero cells, obtained by using a combination of an antibody labeled with compound 17 and an antibody labeled with compound 33. The figures on the right in FIG. 10 are super-resolution images by SMLM, and the figures on the left illustrate averaged images of fluorescence intensity as a comparison.

FIG. 10 illustrates results of SMLM imaging in two colors for mitochondria and microtubules in fixed Vero cells, the imaging performed by using a combination of an antibody labeled with compound 17 and an antibody labeled with compound 33. The figures on the right in FIG. 10 are super-resolution images by SMLM, and the figures on the left illustrate averaged images of fluorescence intensity as a comparison. The antibody labeled with compound 33 stained the microtubules indicated in green, while the antibody labeled with compound 17 stained the mitochondria indicated in red. These images were merged, whereby a super-resolution image was obtained in two colors, indicated in red and green.

The results of FIG. 10 demonstrate that application to two-color super-resolution imaging is made possible by using the two types of probe compounds of the present invention, in which the X atom in formula (I) has been varied.

The invention claimed is:

1. A fluorescent probe for super-resolution imaging comprising a compound represented by formula (I) or a salt thereof (I)

[Chemical formula 1]

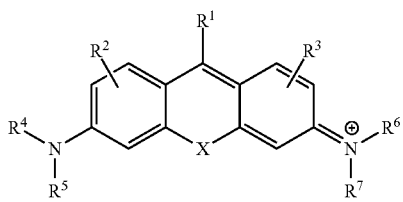

(in the formula, X represents $C(R^a)(R^b)$, or $Si(R^a)(R^b)$ (wherein $R^a$ and $R^b$ each are a methyl group);

$R^1$ represents a hydrogen atom;

$R^2$ and $R^3$ each independently represent one to three identical or differing substituents that are independently selected from the group consisting of a hydrogen atom, a hydroxyl group, a halogen atom, an optionally substituted alkyl group, an optionally substituted sulfo group, an optionally substituted carboxyl group, an optionally substituted ester group, an optionally substituted amide group, and an optionally substituted azide group;

$R^4$ and $R^5$ each independently represent a hydrogen atom or an optionally substituted alkyl group, or $N(R^4)(R^5)$ forms an amide group or a carbamate group (here, when $R^4$ or $R^5$ is an alkyl group, each may form, together with $R^2$, a ring structure that contains a nitrogen atom that is bonded thereto); and $R^6$ and $R^7$ each independently represent a hydrogen atom or an optionally substituted alkyl group, or $N(R^6)(R^7)$ forms an amide group or a carbamate group (here, when $R^6$ or $R^7$ is an alkyl group, each may form, together with $R^3$, a ring structure that contains the nitrogen atom that is bonded thereto), the fluorescent probe for super-resolution imaging being characterized in that the compound represented by formula (I) or the salt thereof undergoes a nucleophilic addition-dissociation equilibrium reaction with a nucleophilic compound that contains a —SH group, wherein a dissociation constant in the nucleophilic addition-dissociation equilibrium reaction is in a range of 0.1 μM to 100 μM.

2. The fluorescent probe for super-resolution imaging according to claim 1, wherein the nucleophilic addition-dissociation equilibrium reaction occurs on a carbon atom to which $R^1$ bonds.

3. The fluorescent probe for super-resolution imaging according to claim 1, characterized in that a nucleophilic addition reaction rate constant in the nucleophilic addition-dissociation equilibrium reaction is 1 to $1.0\times10^6$ s$^{-1}$ in an aqueous solution having neutral conditions.

4. The fluorescent probe for super-resolution imaging according to claim 1, wherein $R^4$, $R^5$, $R^6$, and $R^7$ are each a hydrogen atom.

5. The fluorescent probe for super-resolution imaging according to claim 1, wherein $R^4$, $R^5$, $R^6$, and $R^7$ are each a methyl group.

6. The fluorescent probe for super-resolution imaging according to claim 1, wherein at least one of $R^4$, $R^5$, $R^6$, and $R^7$ has a labeling substituent capable of covalently or non-covalently bonding to a biomolecule.

7. The fluorescent probe for super-resolution imaging according to claim 1, wherein the foregoing compound containing the —SH group has a cysteine residue.

8. The fluorescent probe for super-resolution imaging according to claim 1, wherein the foregoing compound containing the —SH group is glutathione.

9. The fluorescent probe for super-resolution imaging according to claim 1, wherein the compound represented by formula (I) is selected from the following group.

[Chemical formula 2]
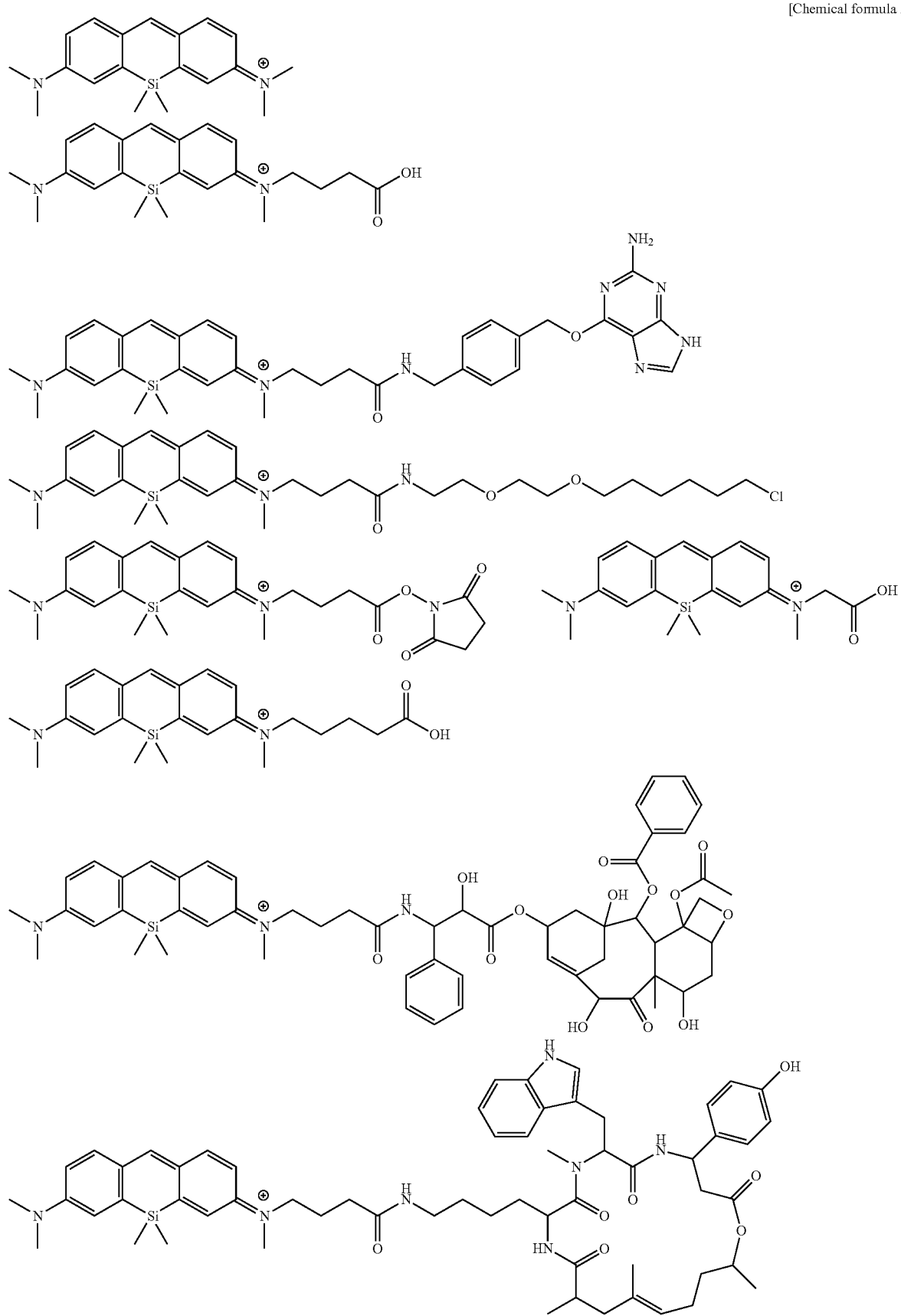

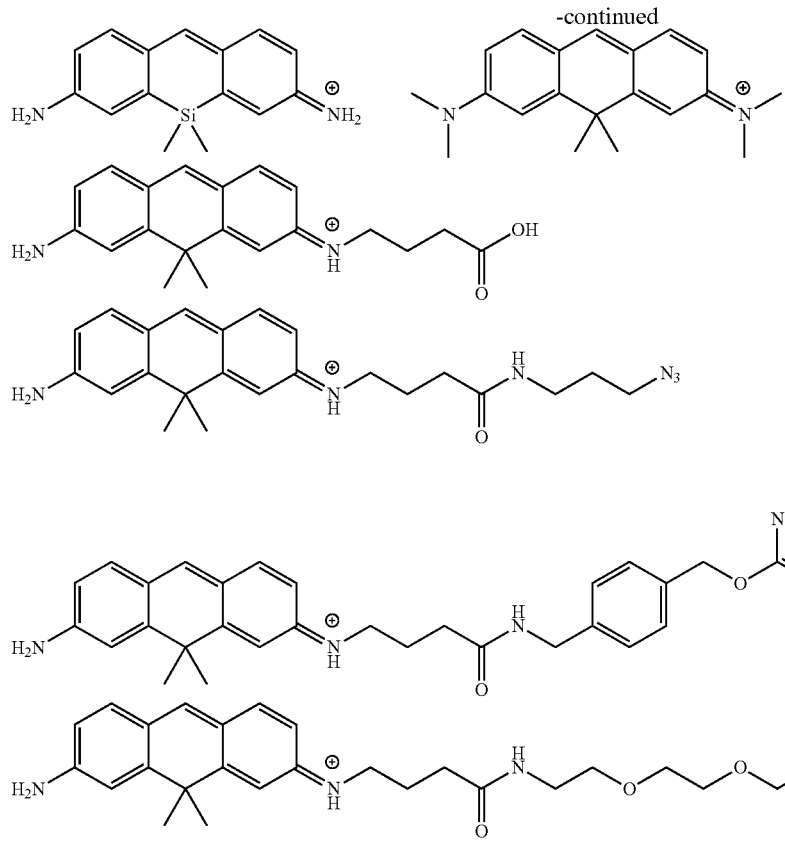

10. A super-resolution fluorescent imaging method using the fluorescent probe for super-resolution imaging according to claim 1, which comprises bonding a probe molecule to a biomolecule, irradiating laser light in the presence of a compound containing a —SH group to acquire image data that have captured fluorescent light emission from the probe molecule, and analyzing and thereafter superimposing a plurality of the image data obtained by repeating the foregoing at a constant time interval to thereby obtain a super-resolution image of a structure of the biomolecule.

* * * * *